United States Patent
Lamser et al.

(10) Patent No.: US 10,317,927 B2
(45) Date of Patent: *Jun. 11, 2019

(54) ENDOSCOPIC CUTTING FORCEPS WITH JAW CLAMP LEVER LATCHING MECHANISM

(71) Applicant: Gyrus ACMI, Inc., Southborough, MA (US)

(72) Inventors: Dennis G. Lamser, Marlborough, MA (US); John R. Mensch, Plymouth, MN (US); Riyad Moe, Madison, WI (US)

(73) Assignee: Gyrus AMCI, Inc., Southborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/817,996

(22) Filed: Nov. 20, 2017

(65) Prior Publication Data

US 2018/0074543 A1     Mar. 15, 2018

Related U.S. Application Data

(63) Continuation of application No. 14/706,146, filed on May 7, 2015, now Pat. No. 9,851,741.

(Continued)

(51) Int. Cl.
*G05G 5/06* (2006.01)
*A61B 17/28* (2006.01)
(Continued)

(52) U.S. Cl.
CPC .......... *G05G 5/005* (2013.01); *A61B 17/295* (2013.01); *A61B 17/2909* (2013.01);
(Continued)

(58) Field of Classification Search
CPC . G05G 5/005; G05G 5/05; G05G 5/06; Y10T 74/20666; A61B 17/295; A61B 17/2841; A61B 17/2909; A61B 2017/2845; A61B 2017/2915; A61B 2017/2916; A61B 2017/2917; A61B 2017/2924; A61B 2017/2946; A61B 18/1445;
(Continued)

(56) References Cited

U.S. PATENT DOCUMENTS 3,189,374 A     6/1965 Mertes
3,694,015 A     9/1972 Gley
(Continued)

FOREIGN PATENT DOCUMENTS

DE     203 05 028     5/2003
DE     10 2012 211200     1/2014
(Continued)

OTHER PUBLICATIONS

Olympus, Halo PKS Cutting Forceps Hand Activation for Laparoscopy & Open, 2011.

*Primary Examiner* — Adam D Rogers
(74) *Attorney, Agent, or Firm* — Pandiscio & Pandiscio

(57) ABSTRACT

A lever latching system comprising: a housing; a lever having a latch pin fixedly mounted to the lever, the lever being movably mounted to the housing so that the latch pin moves in an arc; and a latch plate movably mounted to the housing for linear movement with respect to the housing, the latch plate comprising a labyrinth for receiving the latch pin.

18 Claims, 38 Drawing Sheets

Related U.S. Application Data

(60) Provisional application No. 61/994,179, filed on May 16, 2014.

(51) Int. Cl.
  *G05G 5/00* (2006.01)
  *A61B 17/295* (2006.01)
  *A61B 17/29* (2006.01)
  *A61B 18/14* (2006.01)
  *A61B 18/00* (2006.01)

(52) U.S. Cl.
  CPC ...... *A61B 18/1445* (2013.01); *A61B 18/1447* (2013.01); *A61B 2017/2946* (2013.01); *A61B 2018/00607* (2013.01); *A61B 2018/00916* (2013.01); *A61B 2018/1455* (2013.01)

(58) Field of Classification Search
  CPC ...... A61B 18/1447; A61B 2018/00607; A61B 2018/00916; A61B 2018/1455
  See application file for complete search history.

(56) References Cited

U.S. PATENT DOCUMENTS

| | | | |
|---|---|---|---|
| 3,819,282 A | 6/1974 | Schultz |
| 4,215,884 A | 8/1980 | Little |
| 4,449,022 A | 5/1984 | Uno et al. |
| 4,792,165 A | 12/1988 | Nishimura |
| 5,104,397 A | 4/1992 | Vasconcelos et al. |
| 5,176,702 A | 1/1993 | Bales et al. |
| 5,211,655 A | 5/1993 | Hasson |
| 5,358,292 A | 10/1994 | Van Wiebe et al. |
| 5,425,743 A | 6/1995 | Nicholas |
| 5,498,039 A | 3/1996 | Bivens |
| 5,499,998 A | 3/1996 | Meade |
| 5,735,849 A | 4/1998 | Baden et al. |
| 6,056,333 A | 5/2000 | Wach |
| 6,247,733 B1 | 6/2001 | Weiland |
| 6,585,735 B1 | 7/2003 | Frazier et al. |
| 6,669,250 B1 | 12/2003 | St. Louis |
| 6,799,705 B1 | 10/2004 | Lutoslawski |
| 7,115,139 B2 | 10/2006 | McClurken et al. |
| 7,118,587 B2 | 10/2006 | Dycus et al. |
| 7,150,749 B2 | 12/2006 | Dycus et al. |
| 7,201,411 B2 | 4/2007 | Bella et al. |
| 7,766,910 B2 | 8/2010 | Hixson et al. |
| 7,793,995 B2 | 9/2010 | King et al. |
| 7,802,856 B2 | 9/2010 | Hashemi et al. |
| 8,109,582 B2 | 2/2012 | Dubach |
| 8,398,620 B2 | 3/2013 | Becher et al. |
| 8,945,175 B2 | 2/2015 | Twomey |
| 2006/0190035 A1 | 8/2006 | Hushka et al. |
| 2006/0208506 A1 | 9/2006 | Kern et al. |
| 2011/0112366 A1 | 5/2011 | Bask |
| 2011/0301637 A1 | 12/2011 | Kerr et al. |
| 2012/0109187 A1 | 5/2012 | Gerhardt, Jr. et al. |
| 2012/0184989 A1 | 7/2012 | Twomey |
| 2012/0184990 A1 | 7/2012 | Twomey |
| 2012/0191091 A1 | 7/2012 | Allen |
| 2013/0066317 A1 | 3/2013 | Evans et al. |
| 2013/0325057 A1 | 12/2013 | Larson et al. |
| 2014/0135805 A1 | 5/2014 | Windgassen et al. |
| 2014/0236152 A1 | 8/2014 | Walberg |
| 2016/0338763 A1 | 11/2016 | Allen, IV et al. |
| 2017/0367752 A1* | 12/2017 | Boudreaux ........ A61B 18/1445 |

FOREIGN PATENT DOCUMENTS

| | | |
|---|---|---|
| JP | 3500854 | 2/2004 |
| JP | 2005512606 | 5/2005 |
| JP | 2012148074 | 8/2012 |
| JP | 2013106949 | 6/2013 |

* cited by examiner

Lever closing-
Initial contact between pin on lever and latch pathway

Lever near "latched" position-
As lever rotates inward pin on lever "raises" latch, extending latch spring As lever rotates the pin on the lever does not contact the latch pathway

ENDOSCOPIC CUTTING FORCEPS WITH JAW CLAMP LEVER LATCHING MECHANISM

REFERENCE TO PENDING PRIOR PATENT APPLICATIONS

This patent application is a continuation of pending prior U.S. patent application Ser. No. 14/706,146, filed May 07, 2015 by Gyrus ACMI, Inc., d.b.a. Olympus Surgical Technologies America for ENDOSCOPIC CUTTING FORCEPS WITH JAW CLAMP LEVER LATCHING MECHANISM, which patent application claims benefit of prior U.S. Provisional Patent Application Ser. No. 61/994,179, filed May 16, 2014 by Gyrus ACMI, Inc. (d.b.a. Olympus Surgical Technologies America) and Dennis G. Lamser et al. for ENDOSCOPIC CUTTING FORCEPS WITH JAW CLAMP LEVER LATCHING MECHANISM.

The two (2) above-identified patent applications are hereby incorporated herein by reference.

FIELD OF THE INVENTION

This invention relates to surgical apparatus and methods in general, and more particularly to endoscopic cutting forceps and jaw clamp lever latching mechanisms for use with the same and/or for use with other lever-actuated devices.

BACKGROUND OF THE INVENTION

Endoscopic cutting forceps are well known in the art. In general, endoscopic cutting forceps comprise a pair of jaws disposed at the distal end of a shaft, a blade cutter configured to reciprocate in the space between the jaws (and hence cut tissue disposed between the pair of jaws), and a handle disposed at the proximal end of the shaft for carrying a lever for actuating the pair of jaws and a trigger for actuating the blade cutter. In some constructions, the endoscopic cutting forceps allow the pair of jaws and the blade cutter to be rotated as a unit about the axis of the shaft, and/or the endoscopic cutting forceps allow the pair of jaws to be electrically energized so as to provide electrocautery function to the endoscopic cutting forceps.

In general, it can be convenient to provide a latching mechanism for the lever which actuates the jaws, whereby to allow the jaws to be temporarily locked (or clamped) in a closed position about tissue, e.g., while the blade cutter is actuated to cut the tissue disposed between the clamped jaws.

Unfortunately, current latching mechanisms for endoscopic cutting forceps tend to be mechanically complex and hence difficult and/or expensive to manufacture.

Thus there is a need for a new and improved latching mechanism for an endoscopic cutting forceps wherein the latching mechanism is mechanically simple and hence easy and inexpensive to manufacture.

There is also a need for a new and improved latching mechanism for the actuating levers of other surgical instruments and/or other lever-actuated devices wherein the latching mechanism is mechanically simple and hence easy and inexpensive to manufacture.

SUMMARY OF THE INVENTION

The present invention provides a new and improved latching mechanism for an endoscopic cutting forceps wherein the latching mechanism is mechanically simple and hence easy and inexpensive to manufacture.

The present invention also provides a new and improved latching mechanism for the actuating levers of other surgical instruments and/or other lever-actuated devices wherein the latching mechanism is mechanically simple and hence easy and inexpensive to manufacture.

In one form of the present invention, there is provided a lever latching system comprising:
a housing;
a lever having a latch pin fixedly mounted to said lever, said lever being movably mounted to said housing so that said latch pin moves in an arc; and
a latch plate movably mounted to said housing for linear movement with respect to said housing, said latch plate comprising a labyrinth for receiving said latch pin.

In another form of the present invention, there is provided a lever latching system comprising:
a housing;
a lever pivotally mounted to said housing at a pivot point, and a latch pin fixedly mounted to said lever at a location offset from said pivot point; and
a latch plate movably mounted to said housing for linear movement with respect to said housing, said latch plate comprising a labyrinth for receiving said latch pin.

In another form of the present invention, there is provided a latching system comprising:
a first unit;
a second unit comprising a latch pin, said second unit being movably mounted to said first unit so that said latch pin moves in a prescribed motion;
a selector plate movably mounted to said first unit; and
a latch plate comprising a labyrinth for selectively receiving said latch pin, said latch plate being movably mounted to said selector plate;
wherein said latch plate moves linearly relative to said selector plate.

In another form of the present invention, there is provided a latching system comprising:
a first member;
a second member comprising a latch pin, said second member being movably mounted to said first member so that said latch pin moves in a prescribed motion;
a selector plate movably mounted to said first member;
a latch plate movably mounted to a selector plate and comprising a labyrinth for selectively receiving said latch pin;
a spring secured to said selector plate and engaging said latch plate for biasing said latch plate with respect to said selector plate;
wherein said selector plate moves said latch plate between an engaged position wherein said labyrinth intersects said prescribed motion and a disengaged position wherein said labyrinth does not intersect said prescribed motion.

In another form of the present invention, there is provided a latching system comprising:
a first unit;
a second unit comprising a latch pin, said second unit being movably mounted to said first unit so that said latch pin moves in a prescribed motion;
a selector plate movably mounted to said first unit; and
a latch plate comprising a labyrinth for selectively receiving said latch pin, said latch plate being movably mounted to said selector plate;
wherein said latch plate comprises an integral spring for biasing said latch plate relative to said selector plate.

In another form of the present invention, there is provided a latching system comprising:
a first component comprising a latching pin movable in a prescribed motion; and
a second component comprising a selector plate that moves a latch plate having a labyrinth between an engaged position wherein said labyrinth intersects said prescribed motion and a disengaged position wherein said labyrinth does not intersect said prescribed motion, said second component comprising a latch spring secured to said selector plate for biasing said latch plate with respect to said selector plate.

In another form of the present invention, there is provided a latching system comprising:
a first unit;
a second unit;
said first unit and said second unit being movably mounted relative to one another;
a latch pin fixedly mounted to one of said first unit and said second unit; and
a latch plate movably mounted to the other of said first unit and said second unit for linear movement with respect to said other of said first unit and said second unit, said latch plate comprising a labyrinth for receiving said latch pin.

In another form of the present invention, there is provided a latching system comprising:
a first unit fixedly mounted to a handpiece;
a second unit;
said first unit and said second unit being movably mounted relative to one another;
a latch pin fixedly mounted to one of said first unit and said second unit; and
a latch plate movably mounted to the other of said first unit and said second unit for linear movement with respect to said other of said first unit and said second unit, said latch plate comprising a labyrinth for receiving said latch pin.

In another form of the present invention, there is provided a latching system comprising:
a first unit;
a second unit pivotably mounted to the first unit;
a latch pin fixedly mounted to one of said first unit and said second unit; and
a latch plate movably mounted to the other of said first unit and said second unit for linear movement with respect to said other of said first unit and said second unit, said latch plate comprising a labyrinth for receiving said latch pin.

In another form of the present invention, there is provided a latching system comprising:
a first unit;
a second unit;
said first unit and said second unit being movably mounted relative to one another;
a latch pin fixedly mounted to one of said first unit and said second unit; and
a latch plate movably mounted to the other of said first unit and said second unit for non-linear and non-pivotal movement with respect to said other of said first unit and said second unit, said latch plate comprising a labyrinth for receiving said latch pin.

In another form of the present invention, there is provided a latching system comprising:
a first unit;
a second unit;
said first unit and said second unit being movably mounted relative to one another;
a latch pin fixedly mounted to one of said first unit and said second unit; and
a latch plate movably mounted to the other of said first unit and said second unit for non-pivotal movement with respect to said other of said first unit and said second unit, said latch plate comprising a labyrinth for receiving said latch pin.

In another form of the present invention, there is provided a method for operating a mechanism having a first state and a second state, the method comprising:
providing a lever latching system comprising:
a housing connected to the mechanism to be operated;
a lever connected to the mechanism to be operated and pivotally mounted to said housing at a pivot point, and a latch pin fixedly mounted to said lever at a location offset from said pivot point; and
a latch plate movably mounted to said housing for linear movement with respect to said housing, said latch plate comprising a labyrinth for receiving said latch pin;
moving said lever so that said latch pin causes said latch plate to move with respect to said housing so that said latch pin is disposed at a latched position within said labyrinth, whereby to cause the mechanism to transition from its first state to its second state and maintain the mechanism in its second state; and
moving said lever so that said latch pin moves out of its latched position within said labyrinth, whereby to cause the mechanism to transition from its second state to its first state.

In another form of the present invention, there is provided a method for operating a mechanism having a first state and a second state, the method comprising:
providing a lever latching system comprising:
a housing connected to the mechanism to be operated;
a lever connected to the mechanism to be operated and having a latch pin fixedly mounted to said lever, said lever being movably mounted to said housing so that said latch pin moves in an arc; and
a latch plate movably mounted to said housing for linear movement with respect to said housing, said latch plate comprising a labyrinth for receiving said latch pin;
moving said lever so that said latch pin causes said latch plate to move with respect to said housing so that said latch pin is disposed at a latched position within said labyrinth, whereby to cause the mechanism to transition from its first state to its second state and maintain the mechanism in its second state; and
moving said lever so that said latch pin moves out of its latched position within said labyrinth, whereby to cause the mechanism to transition from its second state to its first state.

In another form of the present invention, there is provided a method for operating a mechanism having a first state and a second state, the method comprising:
providing a latching system comprising:
a first unit connected to the mechanism to be operated;
a second unit connected to the mechanism to be operated and comprising a latch pin, said second unit being movably mounted to said first unit so that said latch pin moves in a prescribed motion;
a selector plate movably mounted to said first unit; and
a latch plate comprising a labyrinth for selectively receiving said latch pin, said latch plate being movably mounted to said selector plate;
wherein said latch plate moves linearly relative to said selector plate;
moving said second unit so that said latch pin causes said latch plate to move with respect to said first unit so that said latch pin is disposed at a latched position within said labyrinth, whereby to cause the mechanism to transition from its first state to its second state and maintain the mechanism in its second state; and moving said second unit so that said latch pin moves out of its latched position within said labyrinth, whereby to cause the mechanism to transition from its second state to its first state.

In another form of the present invention, there is provided a method for operating a mechanism having a first state and a second state, the method comprising:

providing a latching system comprising:
a first unit connected to the mechanism to be operated;
a second unit connected to the mechanism to be operated and comprising a latch pin, said second unit being movably mounted to said first unit so that said latch pin moves in a prescribed motion;
a selector plate movably mounted to said first unit; and
a latch plate comprising a labyrinth for selectively receiving said latch pin, said latch plate being movably mounted to said selector plate;
wherein said latch plate comprises an integral spring for biasing said latch plate relative to said selector plate;

moving said second unit so that said latch pin causes said latch plate to move with respect to said first unit so that said latch pin is disposed at a latched position within said labyrinth, whereby to cause the mechanism to transition from its first state to its second state and maintain the mechanism in its second state; and moving said second unit so that said latch pin moves out of its latched position within said labyrinth, whereby to cause the mechanism to transition from its second state to its first state.

In another form of the present invention, there is provided a method for operating a mechanism having a first state and a second state, the method comprising:

providing a latching system comprising:
a first member connected to the mechanism to be operated;
a second member connected to the mechanism to be operated and comprising a latch pin, said second member being movably mounted to said first member so that said latch pin moves in a prescribed motion;
a selector plate movably mounted to said first member;
a latch plate movably mounted to a selector plate and comprising a labyrinth for selectively receiving said latch pin;
a spring secured to said selector plate and engaging said latch plate for biasing said latch plate with respect to said selector plate;
wherein said selector plate moves said latch plate between an engaged position wherein said labyrinth intersects said prescribed motion and a disengaged position wherein said labyrinth does not intersect said prescribed motion;

moving said second member so that said latch pin causes said latch plate to move with respect to said first member so that said latch pin is disposed at a latched position within said labyrinth, whereby to cause the mechanism to transition from its first state to its second state and maintain the mechanism in its second state; and moving said second member so that said latch pin moves out of its latched position within said labyrinth, whereby to cause the mechanism to transition from its second state to its first state.

In another form of the present invention, there is provided a method for operating a mechanism having a first state and a second state, the method comprising:

providing a latching system comprising:

a first component connected to the mechanism to be operated and comprising a latching pin movable in a prescribed motion; and
a second component connected to the mechanism to be operated and comprising a selector plate that moves a latch plate having a labyrinth between an engaged position wherein said labyrinth intersects said prescribed motion and a disengaged position wherein said labyrinth does not intersect said prescribed motion, said second component comprising a latch spring secured to said selector plate for biasing said latch plate with respect to said selector plate;

moving said first component so that said latching pin causes said latch plate to move with respect to said second component so that said latching pin is disposed at a latched position within said labyrinth, whereby to cause the mechanism to transition from its first state to its second state and maintain the mechanism in its second state; and moving said first component so that said latching pin moves out of its latched position within said labyrinth, whereby to cause the mechanism to transition from its second state to its first state.

In another form of the present invention, there is provided a method for operating a mechanism having a first state and a second state, the method comprising:

providing a latching system comprising:
a first unit connected to the mechanism to be operated;
a second unit connected to the mechanism to be operated;
said first unit and said second unit being movably mounted relative to one another;
a latch pin fixedly mounted to one of said first unit and said second unit; and
a latch plate movably mounted to the other of said first unit and said second unit for linear movement with respect to said other of said first unit and said second unit, said latch plate comprising a labyrinth for receiving said latch pin;

moving one of said first unit and said second unit so that said latch pin causes said latch plate to move with respect to the other of said first unit and said second unit so that said latch pin is disposed at a latched position within said labyrinth, whereby to cause the mechanism to transition from its first state to its second state and maintain the mechanism in its second state; and moving one of said first unit and said second unit so that said latch pin moves out of its latched position within said labyrinth, whereby to cause the mechanism to transition from its second state to its first state.

In another form of the present invention, there is provided a method for operating a mechanism having a first state and a second state, the method comprising:

providing a latching system comprising:
a first unit connected to the mechanism to be operated and fixedly mounted to a handpiece;
a second unit connected to the mechanism to be operated;
said first unit and said second unit being movably mounted relative to one another;
a latch pin fixedly mounted to one of said first unit and said second unit; and
a latch plate movably mounted to the other of said first unit and said second unit for linear movement with respect to said other of said first unit and said second unit, said latch plate comprising a labyrinth for receiving said latch pin;

moving one of said first unit and said second unit so that said latch pin causes said latch plate to move with respect to the other of said first unit and said second unit so that said latch pin is disposed at a latched position within said labyrinth, whereby to cause the mechanism to transition from its first state to its second state and maintain the mechanism in its second state; and moving one of said first unit and said second unit so that said latch pin moves out of its latched position within said labyrinth, whereby to cause the mechanism to transition from its second state to its first state.

In another form of the present invention, there is provided a method for operating a mechanism having a first state and a second state, the method comprising:

providing a latching system comprising:
a first unit connected to the mechanism to be operated;
a second unit connected to the mechanism to be operated and pivotably mounted to the first unit;
a latch pin fixedly mounted to one of said first unit and said second unit; and
a latch plate movably mounted to the other of said first unit and said second unit for linear movement with respect to said other of said first unit and said second unit, said latch plate comprising a labyrinth for receiving said latch pin;

moving one of said first unit and said second unit so that said latch pin causes said latch plate to move with respect to the other of said first unit and said second unit so that said latch pin is disposed at a latched position within said labyrinth, whereby to cause the mechanism to transition from its first state to its second state and maintain the mechanism in its second state; and moving one of said first unit and said second unit so that said latch pin moves out of its latched position within said labyrinth, whereby to cause the mechanism to transition from its second state to its first state.

In another form of the present invention, there is provided a method for operating a mechanism having a first state and a second state, the method comprising:

providing a latching system comprising:
a first unit connected to the mechanism to be operated;
a second unit connected to the mechanism to be operated;
said first unit and said second unit being movably mounted relative to one another;
a latch pin fixedly mounted to one of said first unit and said second unit; and
a latch plate movably mounted to the other of said first unit and said second unit for non-linear and non-pivotal movement with respect to said other of said first unit and said second unit, said latch plate comprising a labyrinth for receiving said latch pin;

moving one of said first unit and said second unit so that said latch pin causes said latch plate to move with respect to the other of said first unit and said second unit so that said latch pin is disposed at a latched position within said labyrinth, whereby to cause the mechanism to transition from its first state to its second state and maintain the mechanism in its second state; and moving one of said first unit and said second unit so that said latch pin moves out of its latched position within said labyrinth, whereby to cause the mechanism to transition from its second state to its first state.

In another form of the present invention, there is provided a method for operating a mechanism having a first state and a second state, the method comprising:

providing a latching system comprising:
a first unit connected to the mechanism to be operated;
a second unit connected to the mechanism to be operated;
said first unit and said second unit being movably mounted relative to one another;
a latch pin fixedly mounted to one of said first unit and said second unit; and
a latch plate movably mounted to the other of said first unit and said second unit for non-pivotal movement with respect to said other of said first unit and said second unit, said latch plate comprising a labyrinth for receiving said latch pin;

moving one of said first unit and said second unit so that said latch pin causes said latch plate to move with respect to the other of said first unit and said second unit so that said latch pin is disposed at a latched position within said labyrinth, whereby to cause the mechanism to transition from its first state to its second state and maintain the mechanism in its second state; and moving one of said first unit and said second unit so that said latch pin moves out of its latched position within said labyrinth, whereby to cause the mechanism to transition from its second state to its first state.

In another form of the present invention, there is provided a latching system comprising:

a first unit;
a second unit comprising a latch pin, said second unit being movably mounted to said first unit so that said latch pin moves in a prescribed motion;
a selector plate movably mounted to said first unit; and
a latch plate comprising a labyrinth for selectively receiving said latch pin, said latch plate being movably mounted to said selector plate;
wherein said latch plate comprises an integral spring for biasing said latch plate relative to said first unit.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
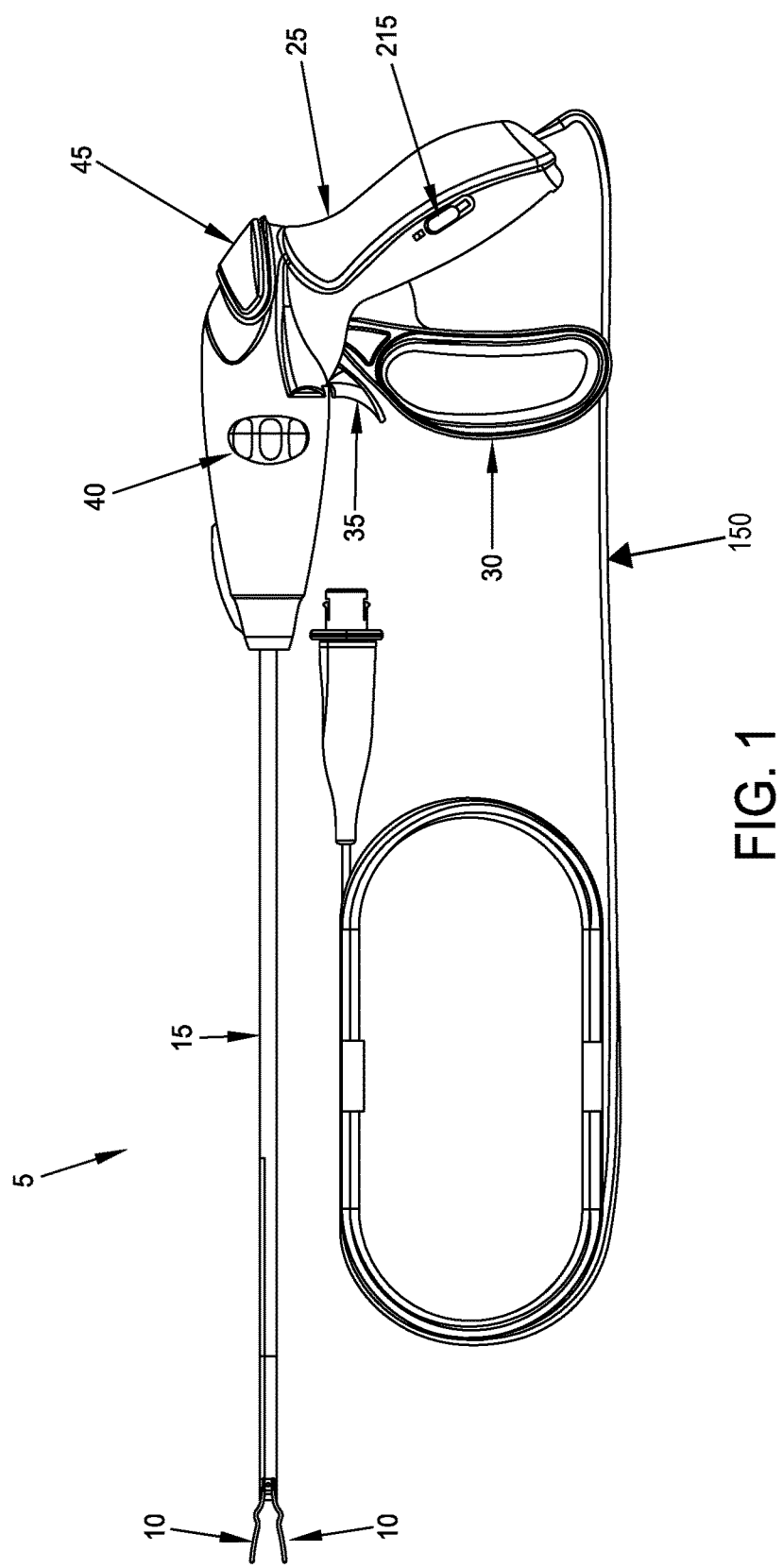
FIGS. 1-26 are schematic views showing a novel endoscopic cutting forceps formed in accordance with the present invention, wherein the novel endoscopic cutting forceps comprise a novel jaw clamp lever latching mechanism formed in accordance with the present invention, with FIGS. 1-16 generally showing the general features of the novel endoscopic cutting forceps and FIGS. 17-26 generally showing the novel jaw clamp lever latching mechanism of the novel endoscopic cutting forceps.
Figure 2:
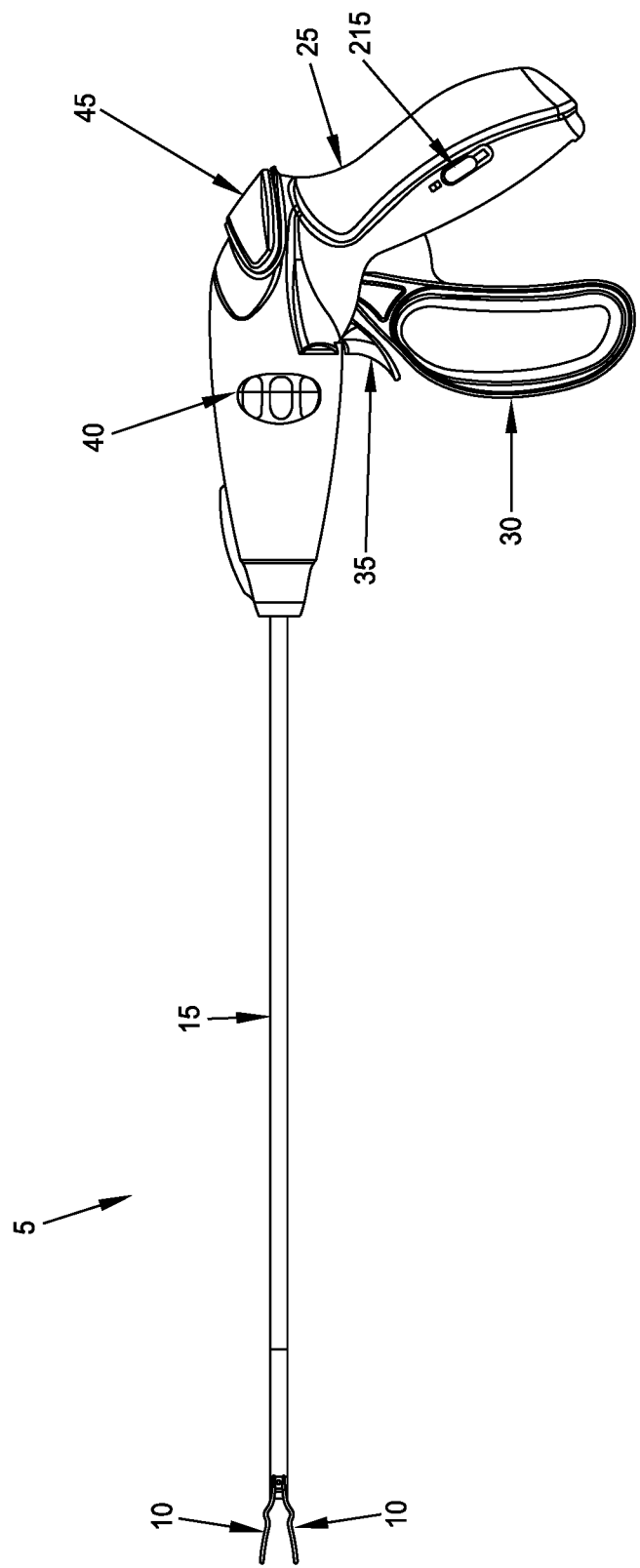
Figure 3:
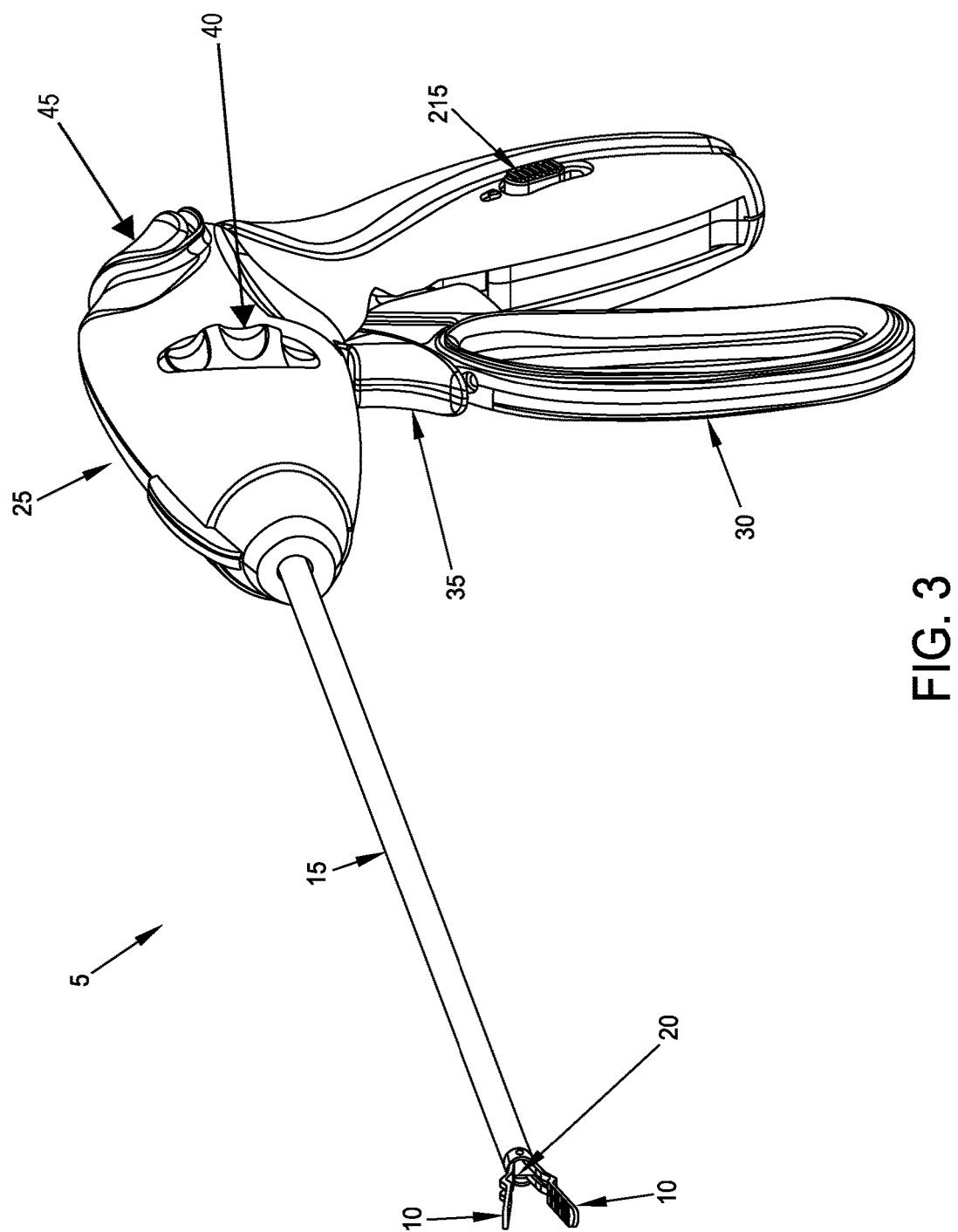
Figure 4:
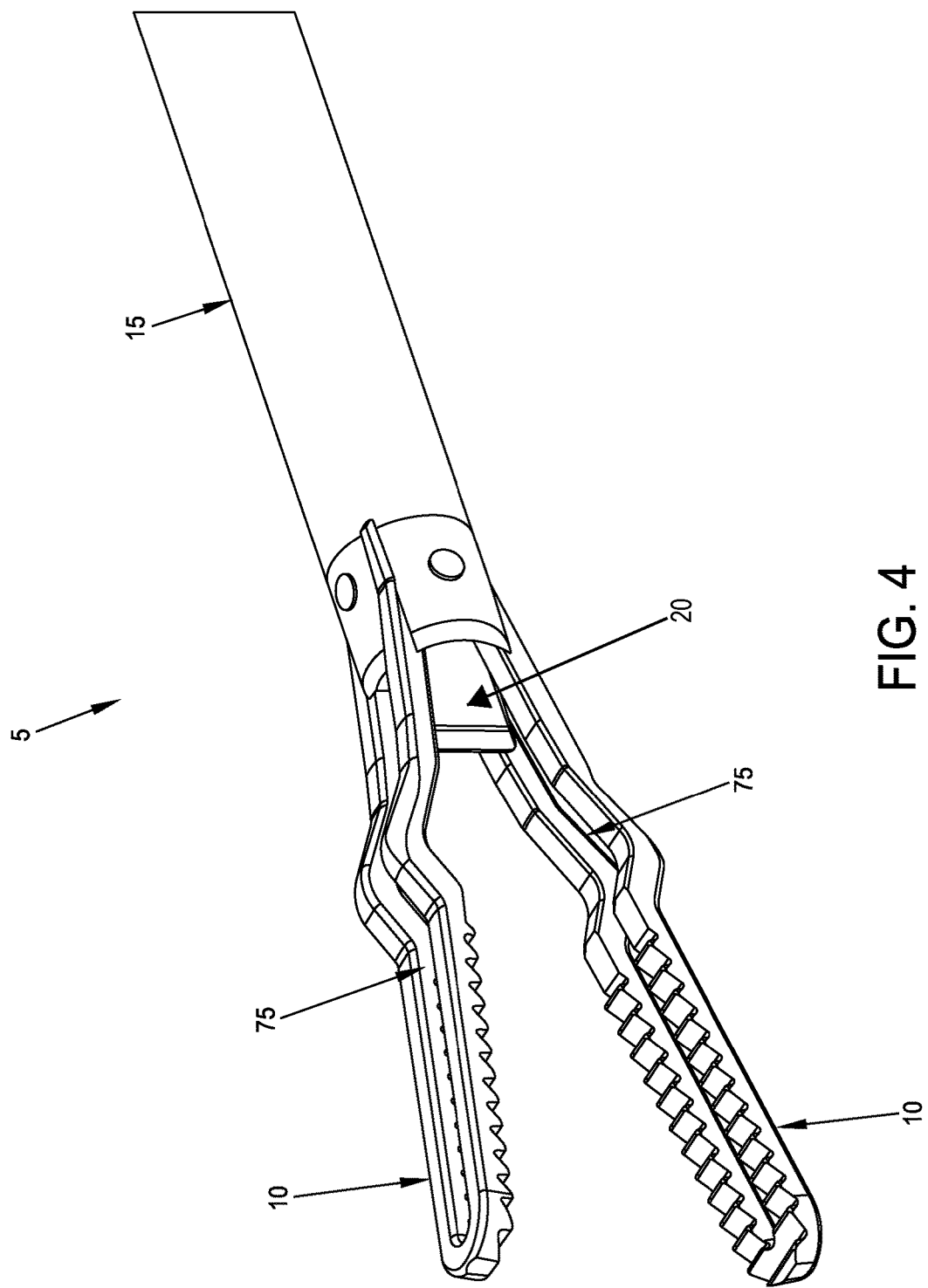
Figure 5:
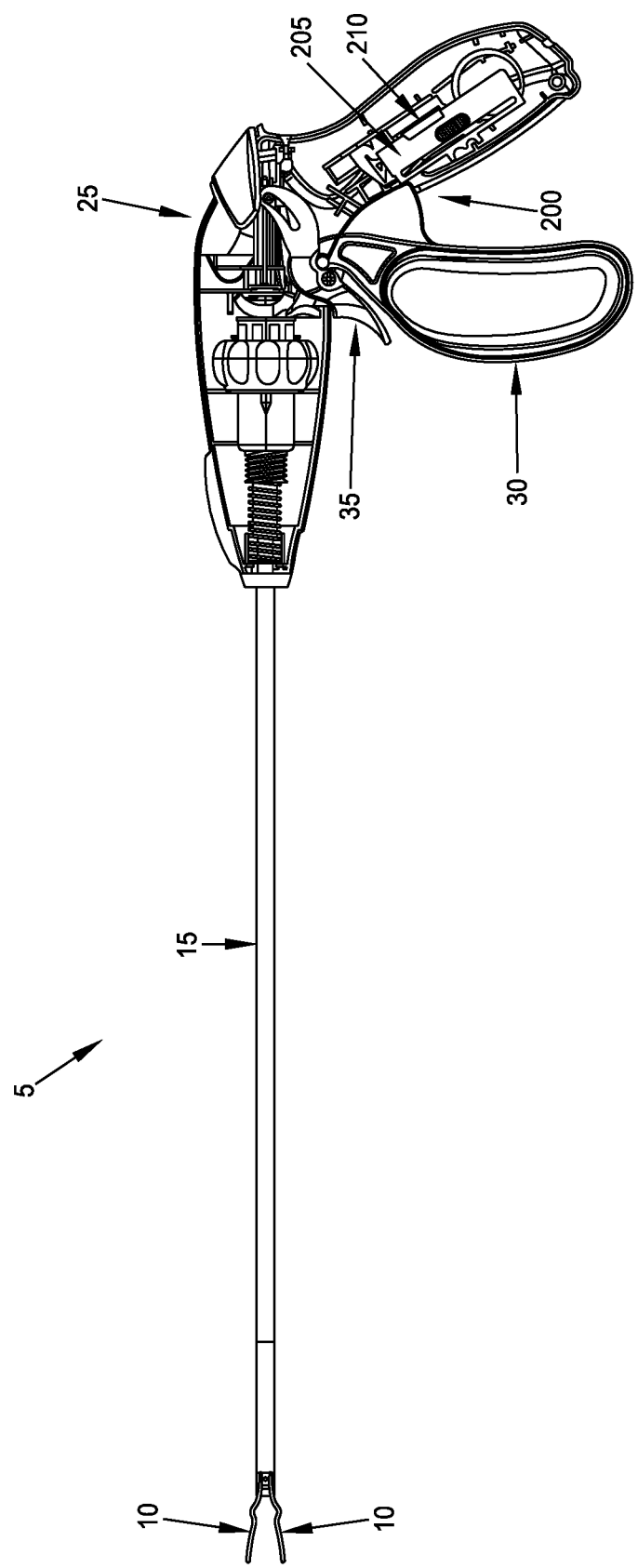
Figure 6:
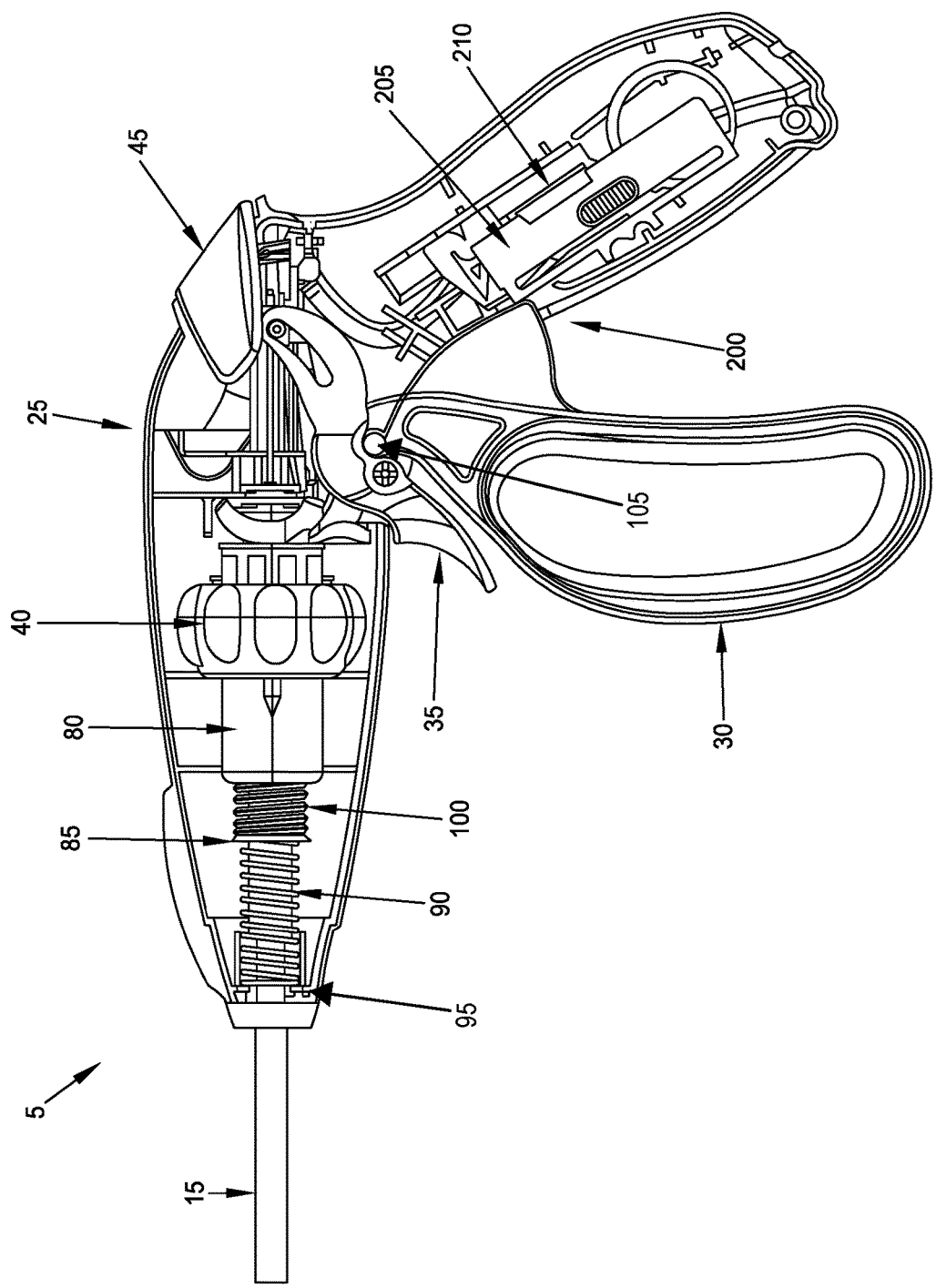
Figure 7:
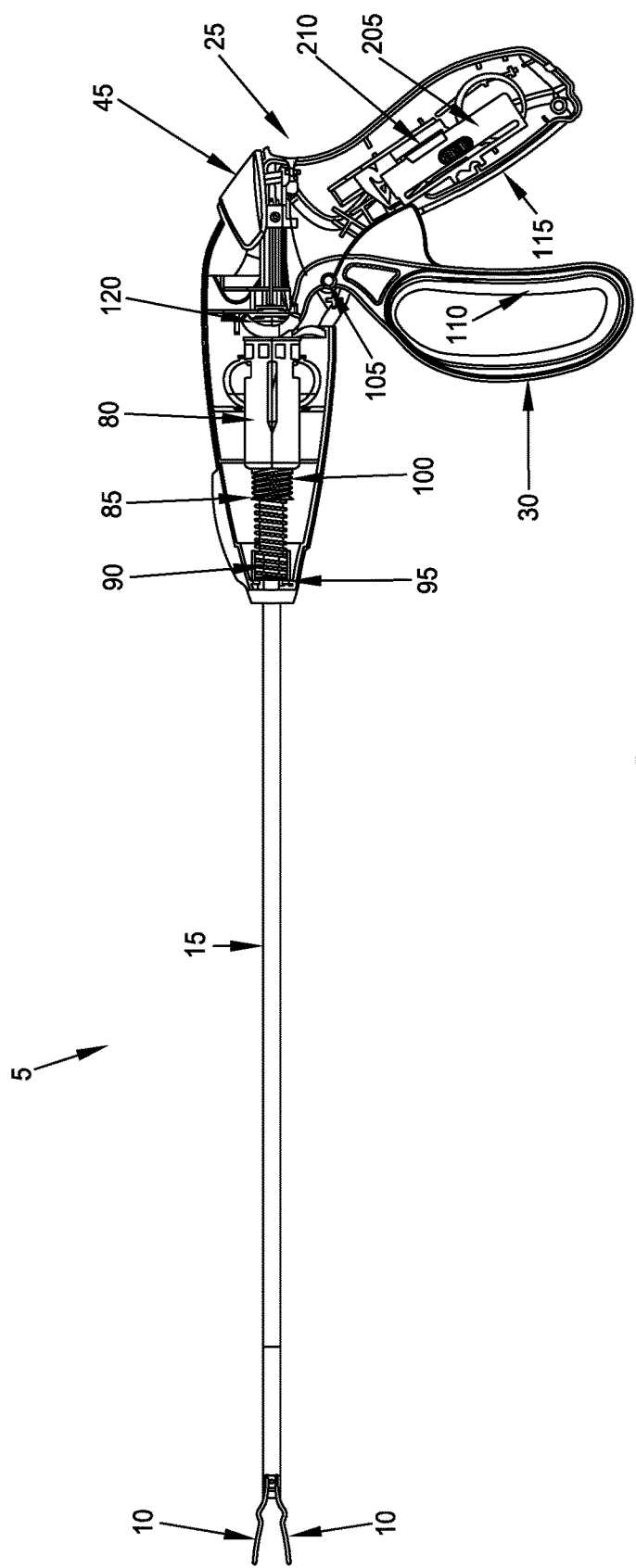
Figure 8:
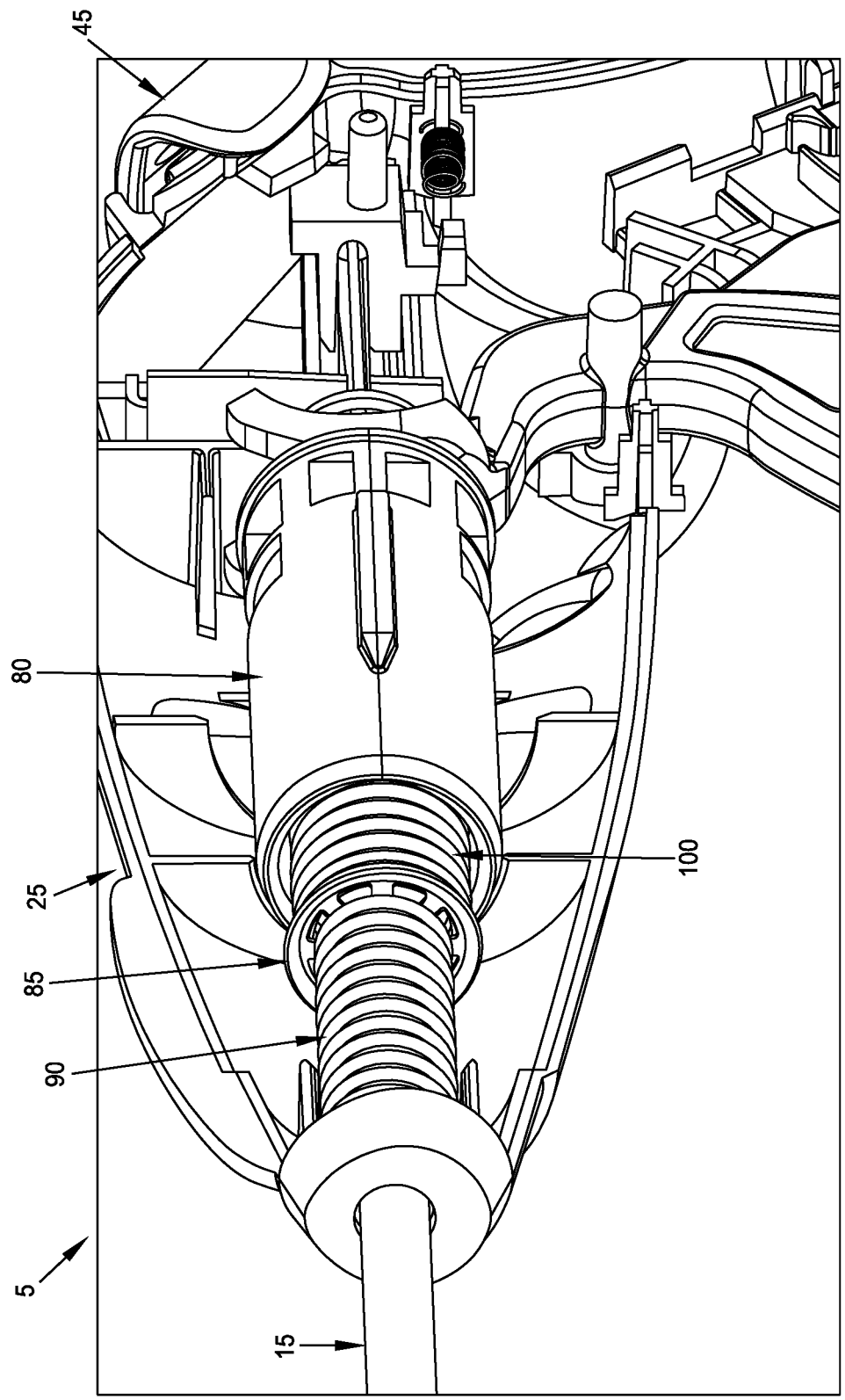
Figure 9:
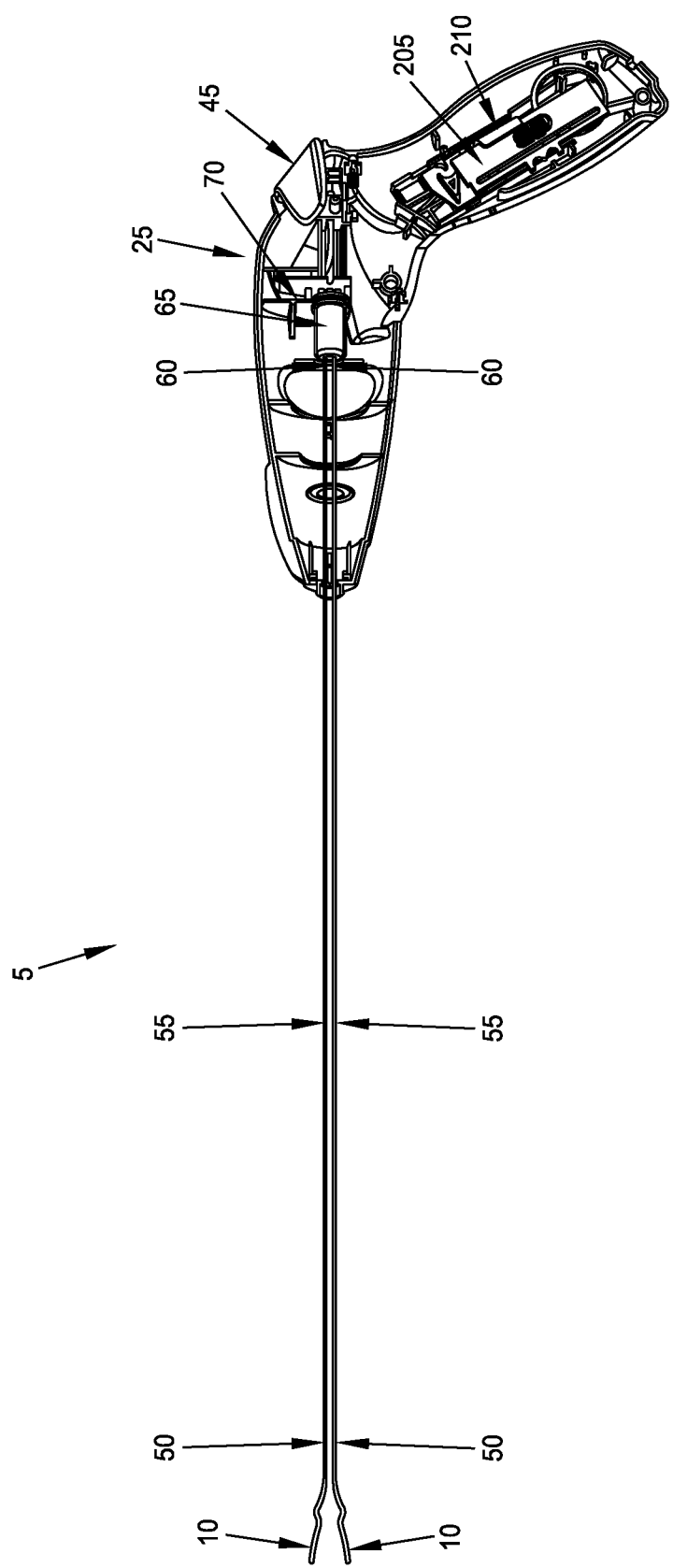
Figure 10:
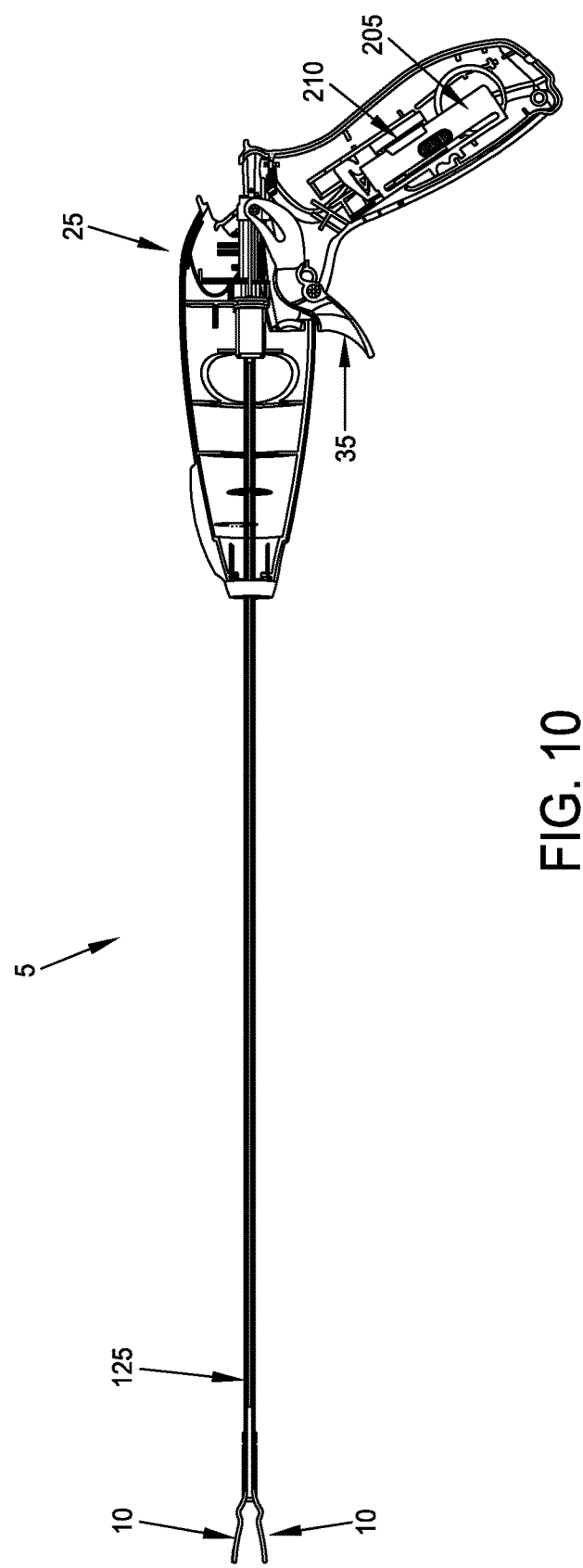
Figure 11:
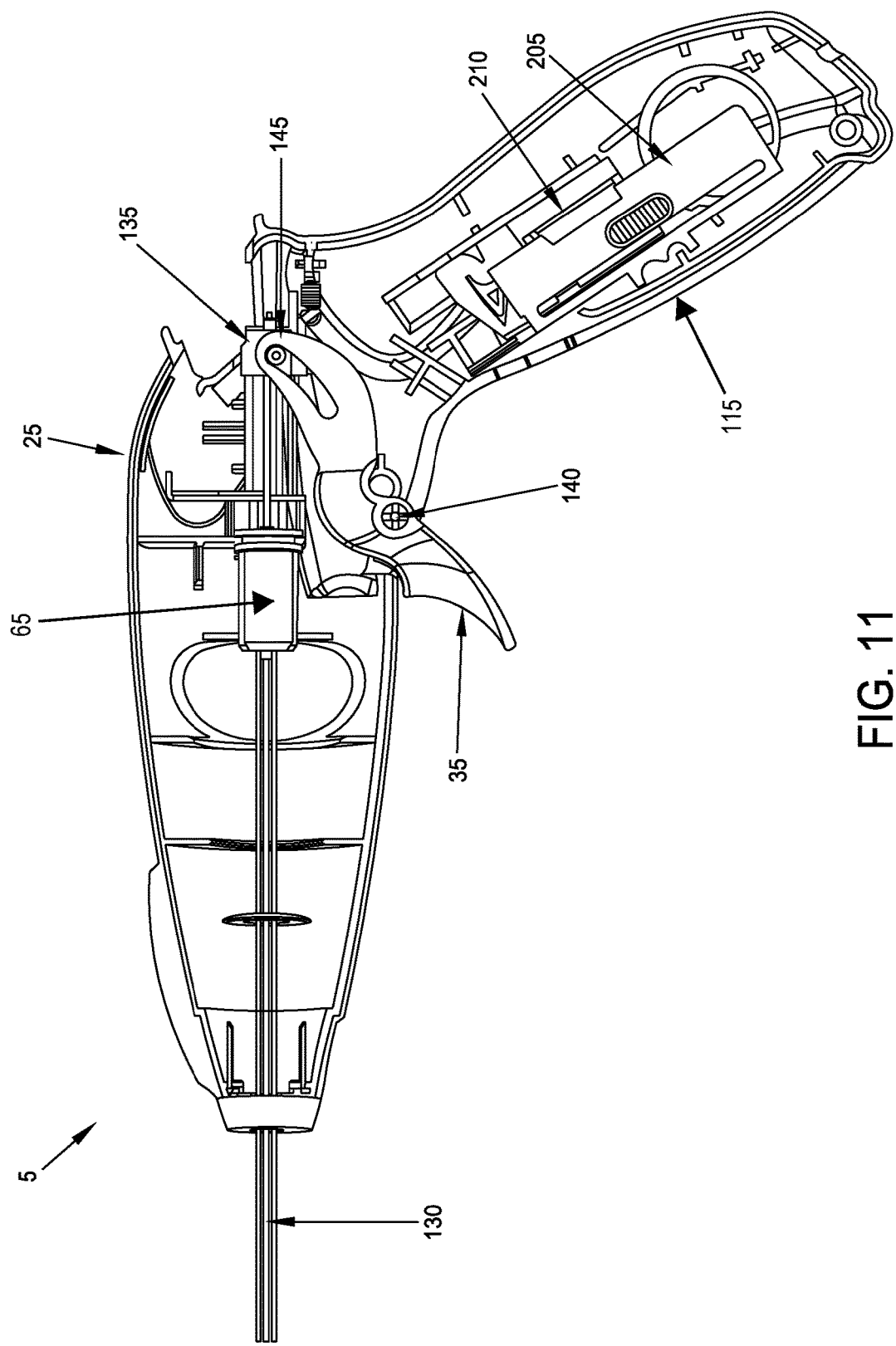
Figure 12:
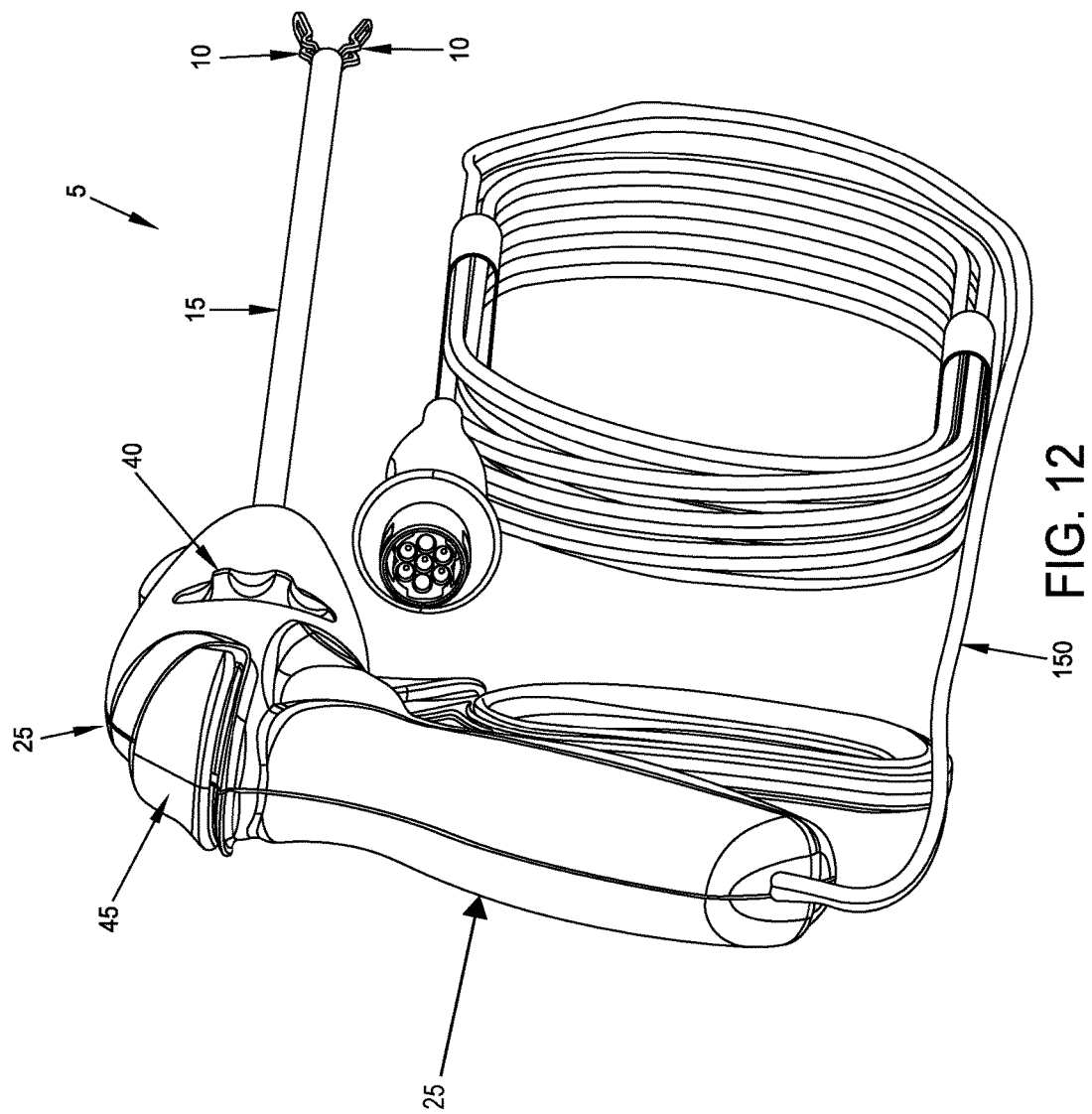
Figure 13:
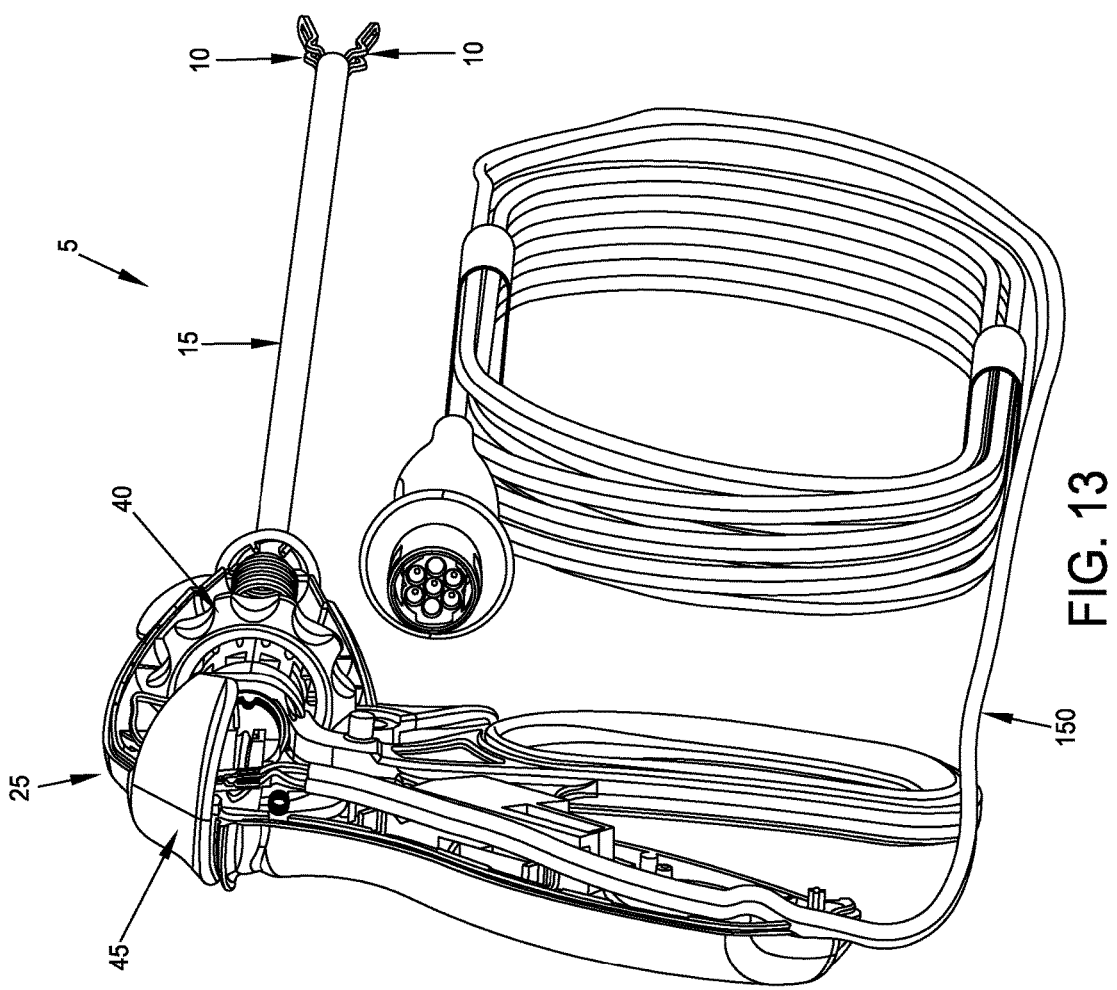
Figure 14:
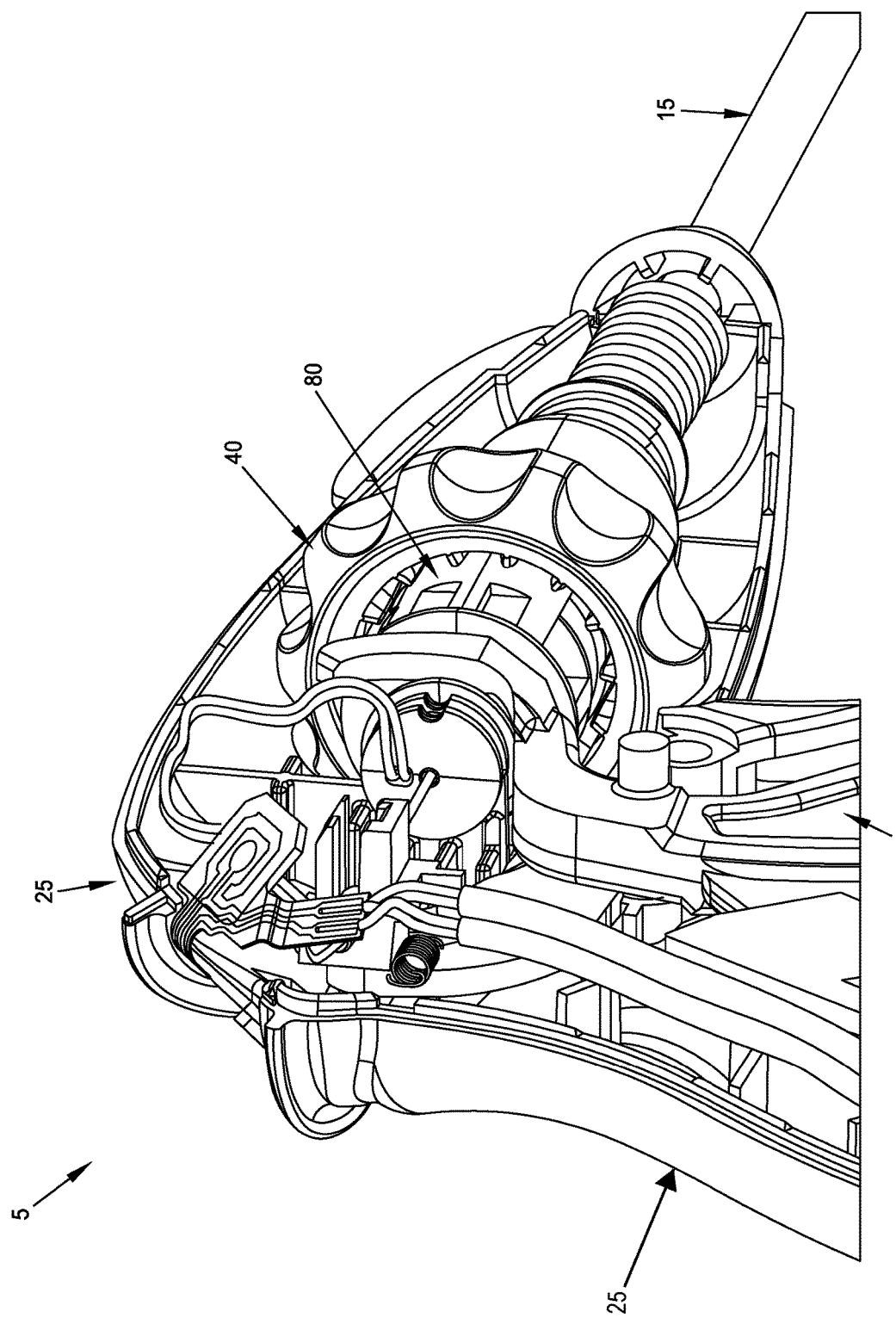
Figure 15:
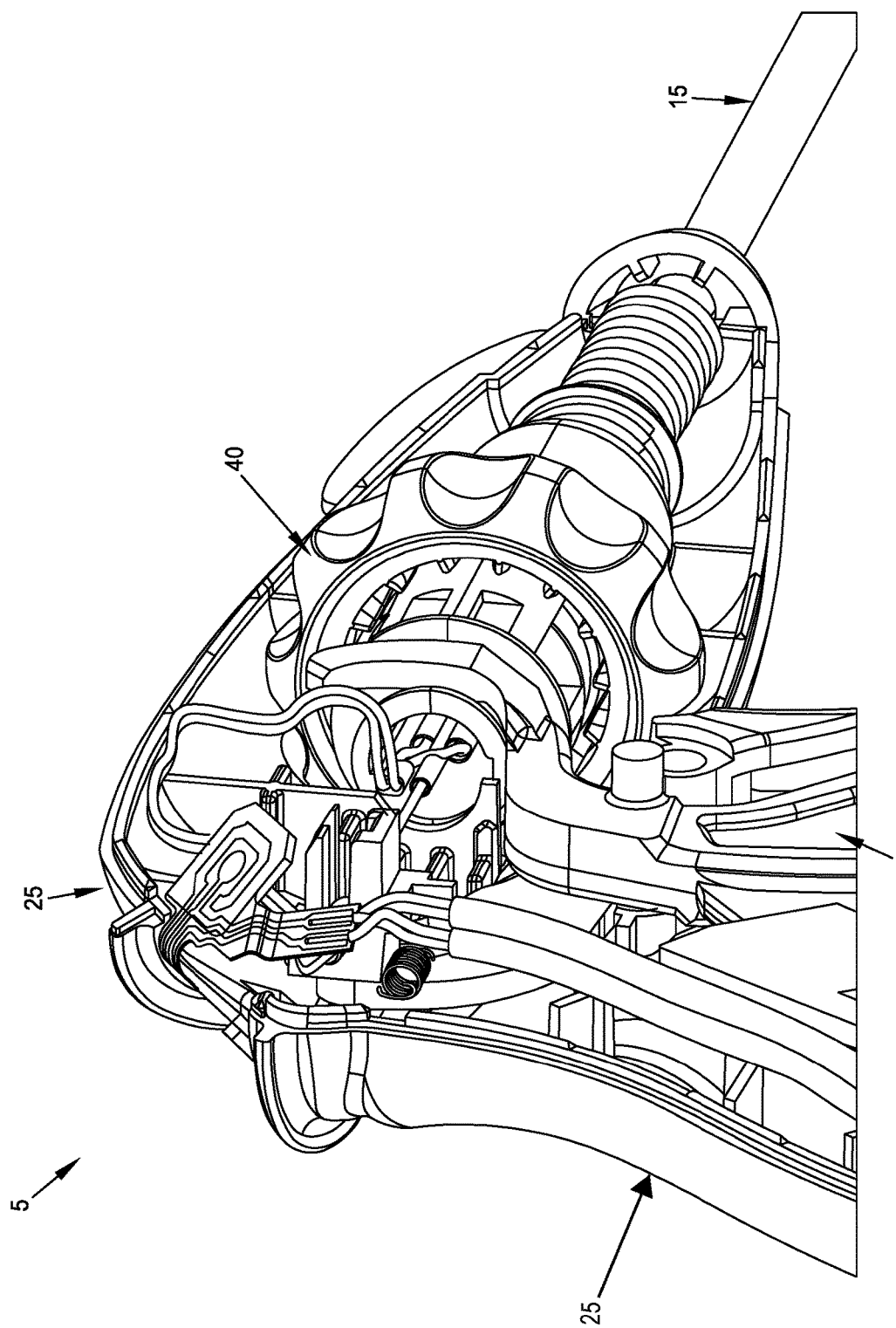
Figure 16:
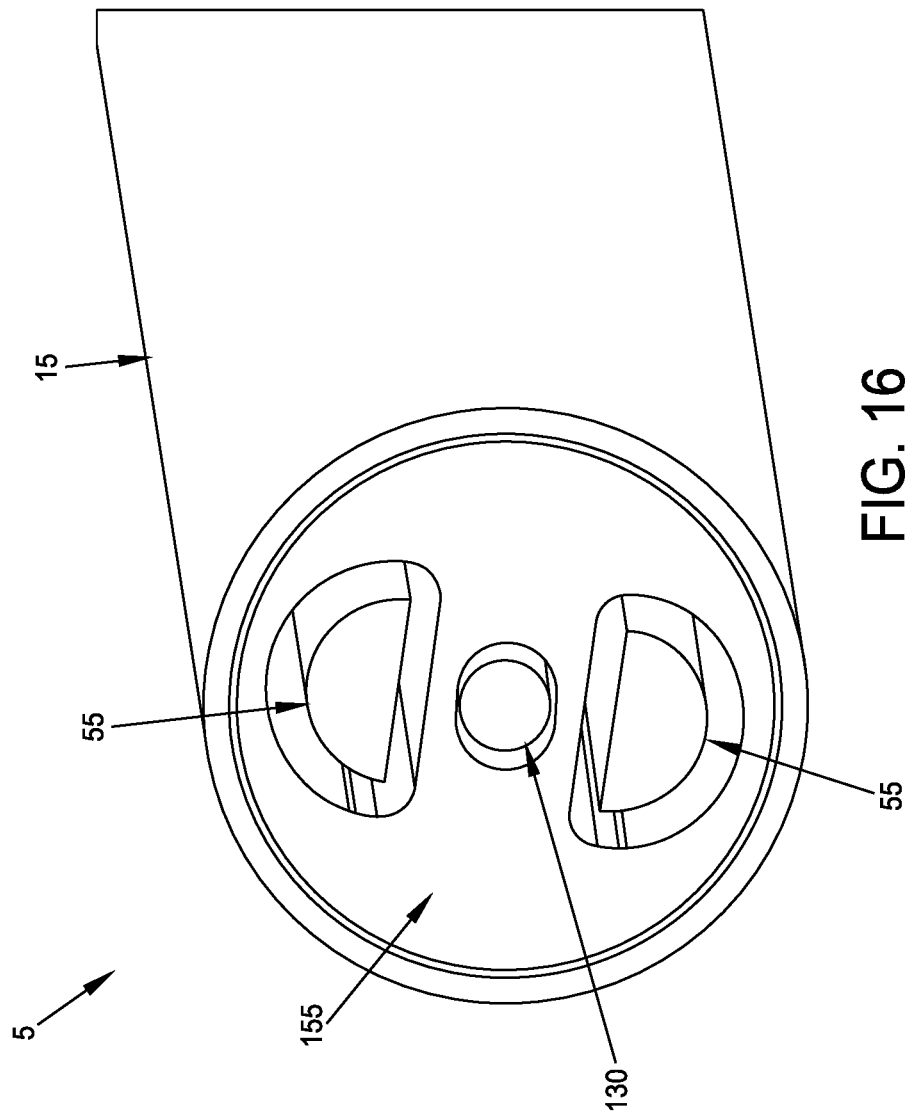
Figure 17:
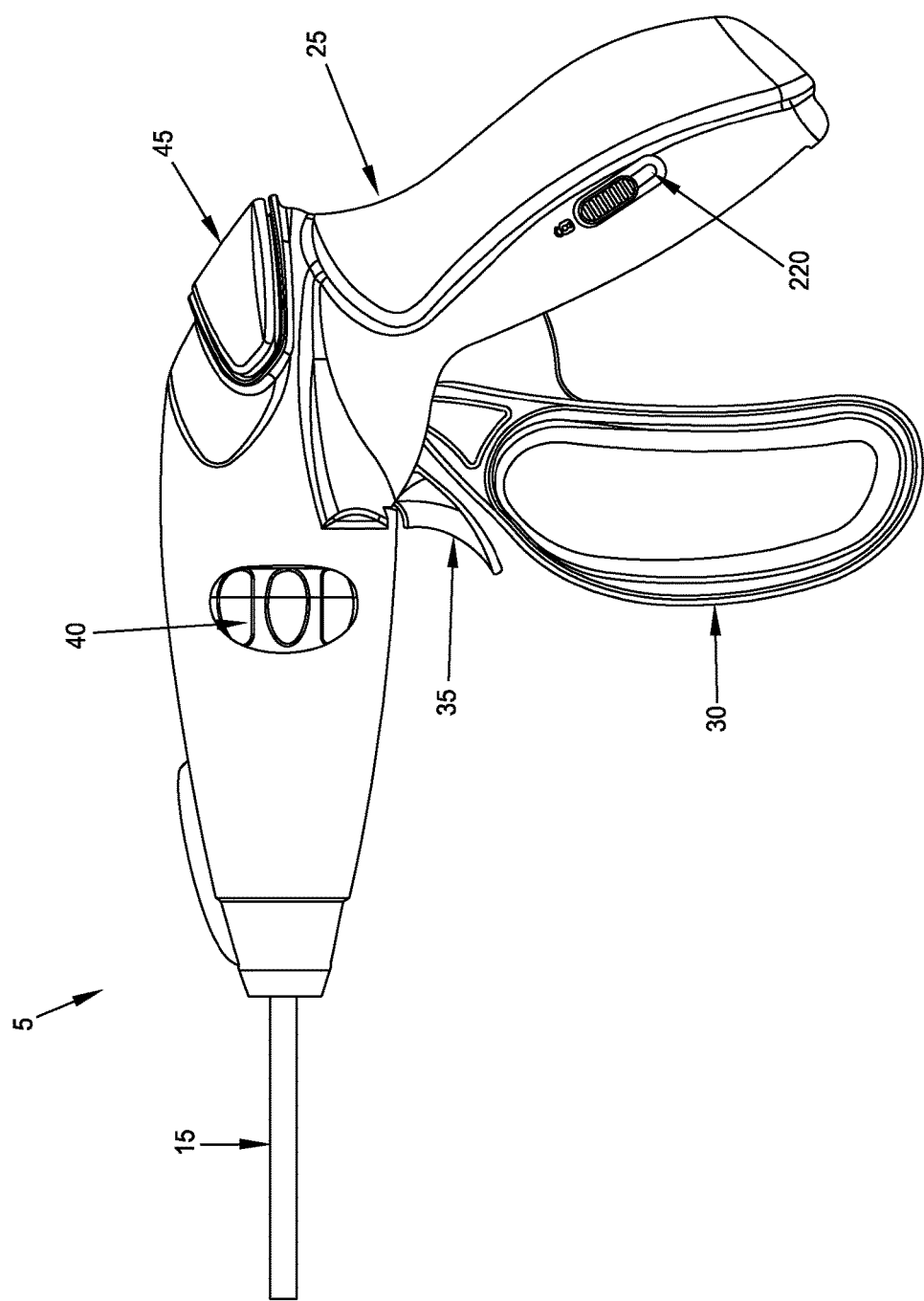
Figure 18:
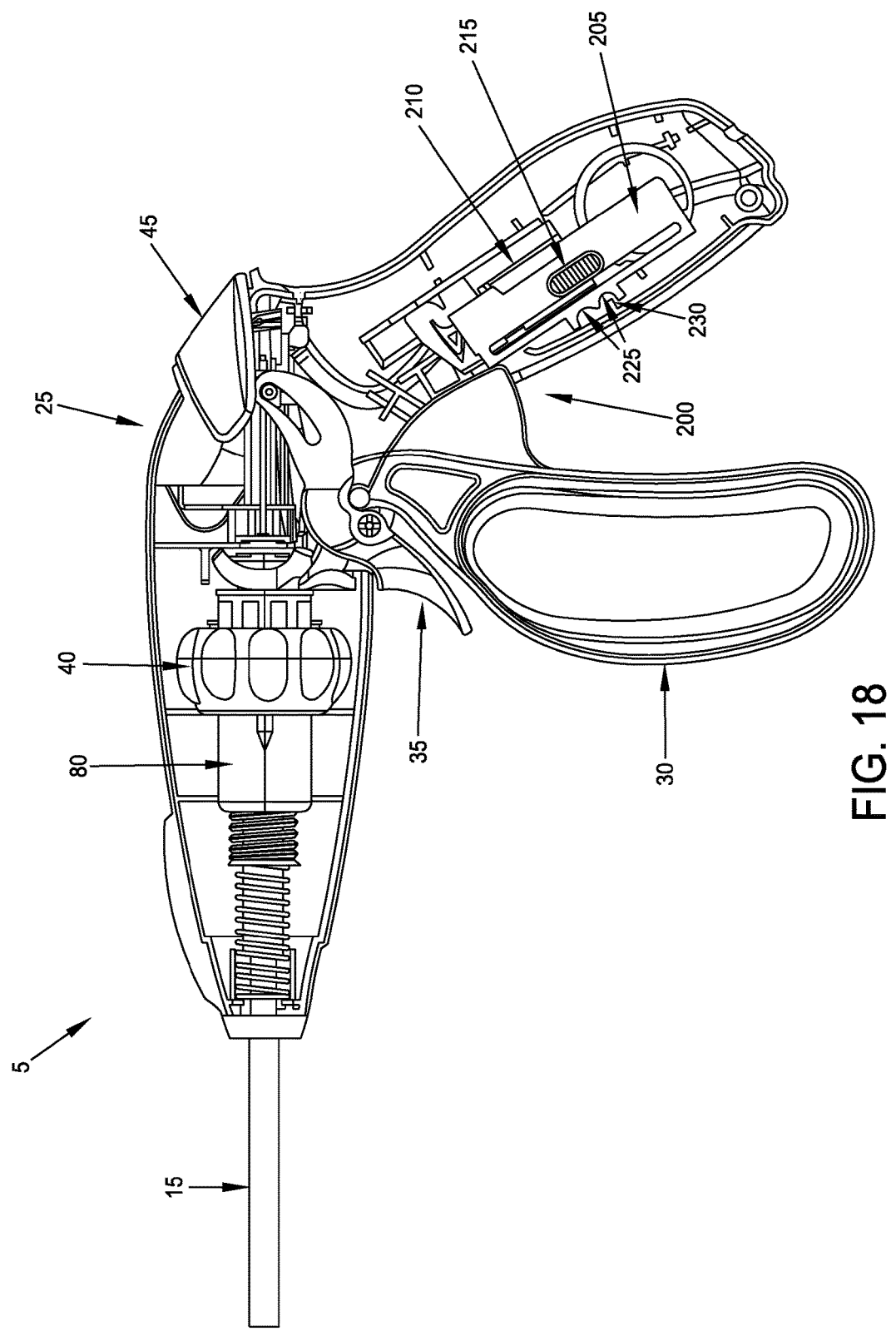
Figure 19:
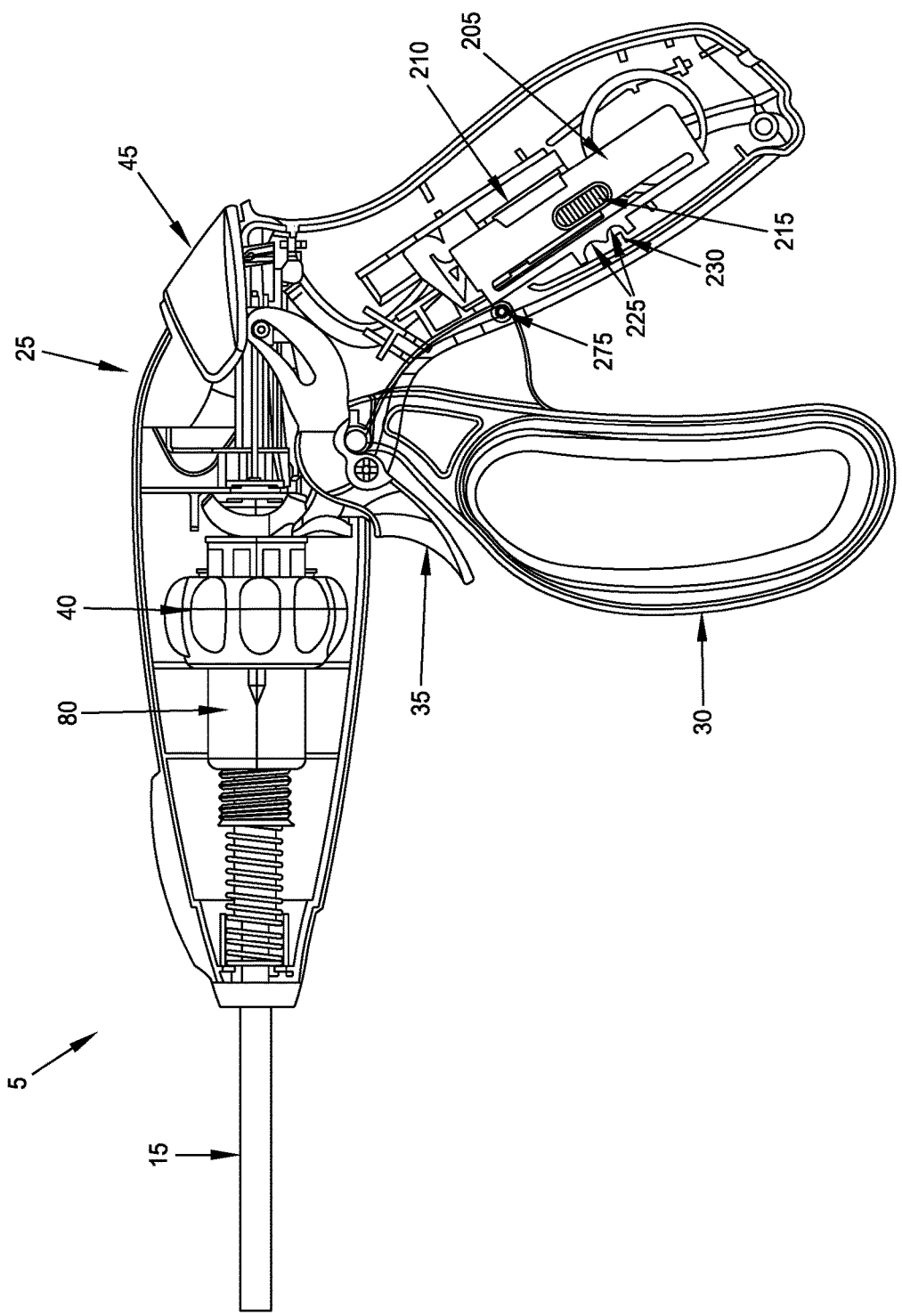
Figure 20:
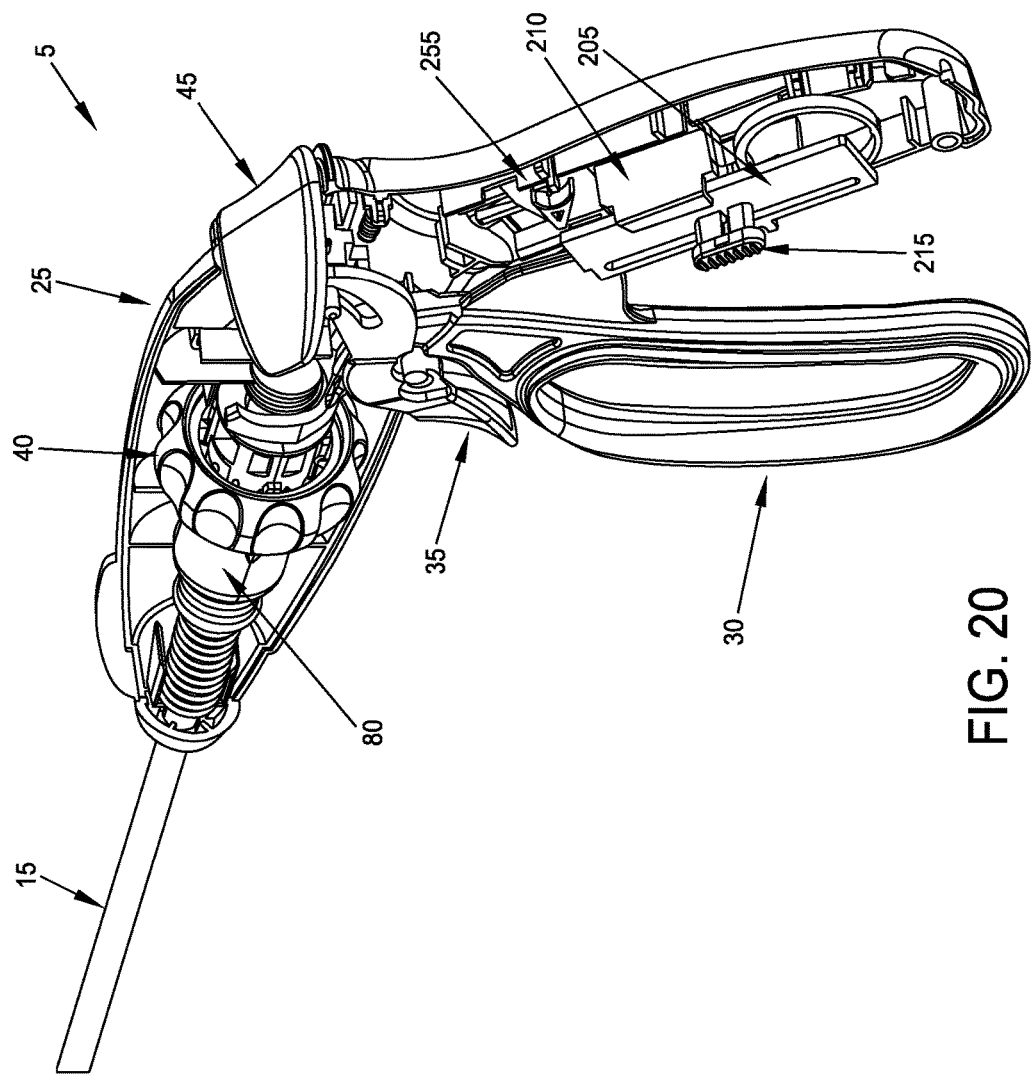
Figure 21:
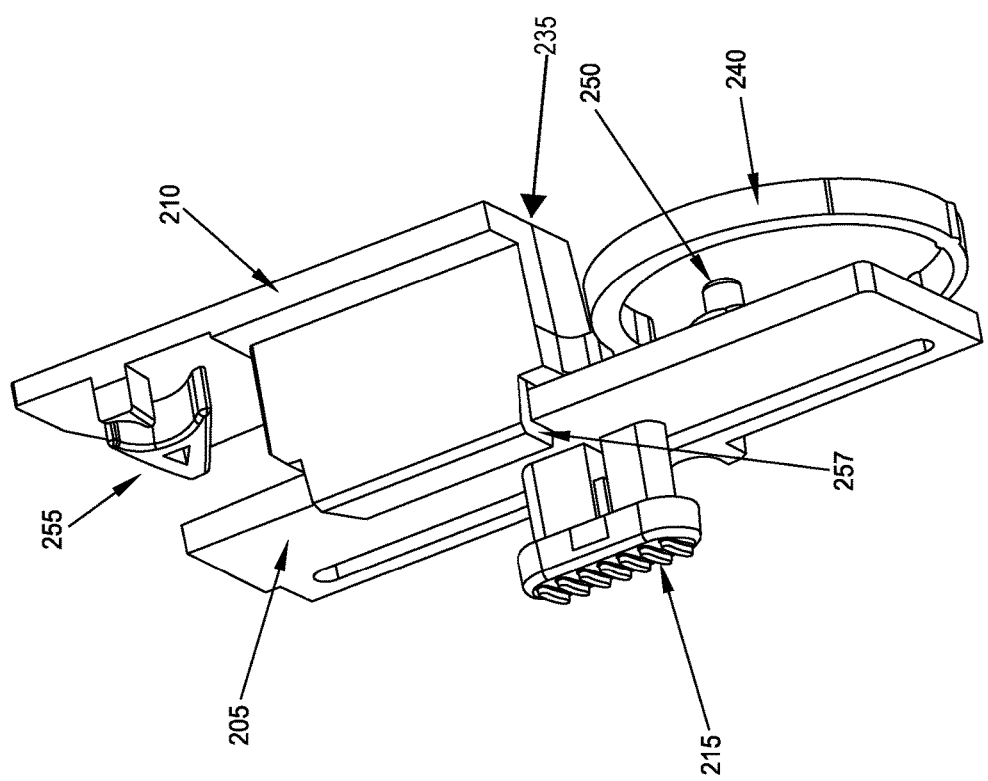
Figure 22:
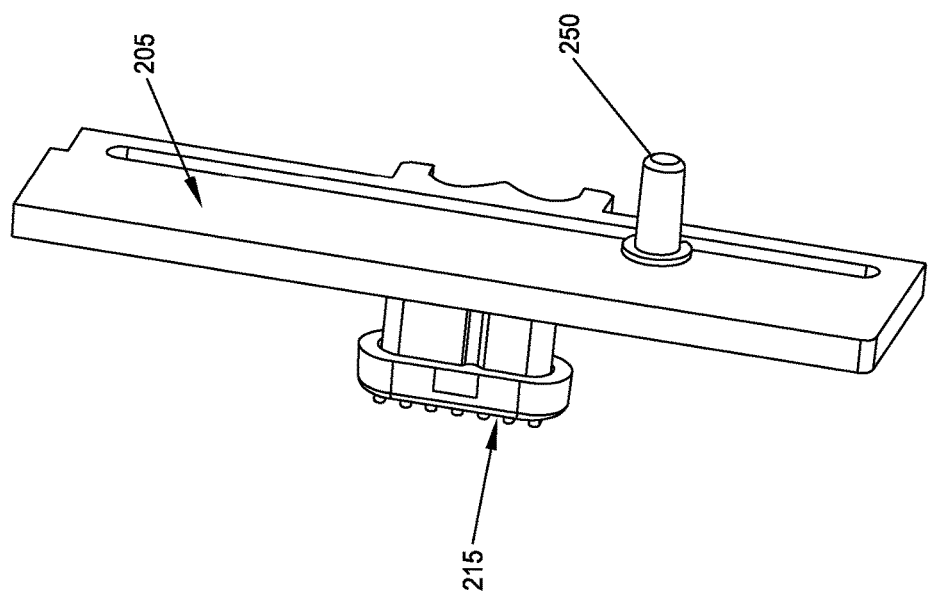
Figure 23:
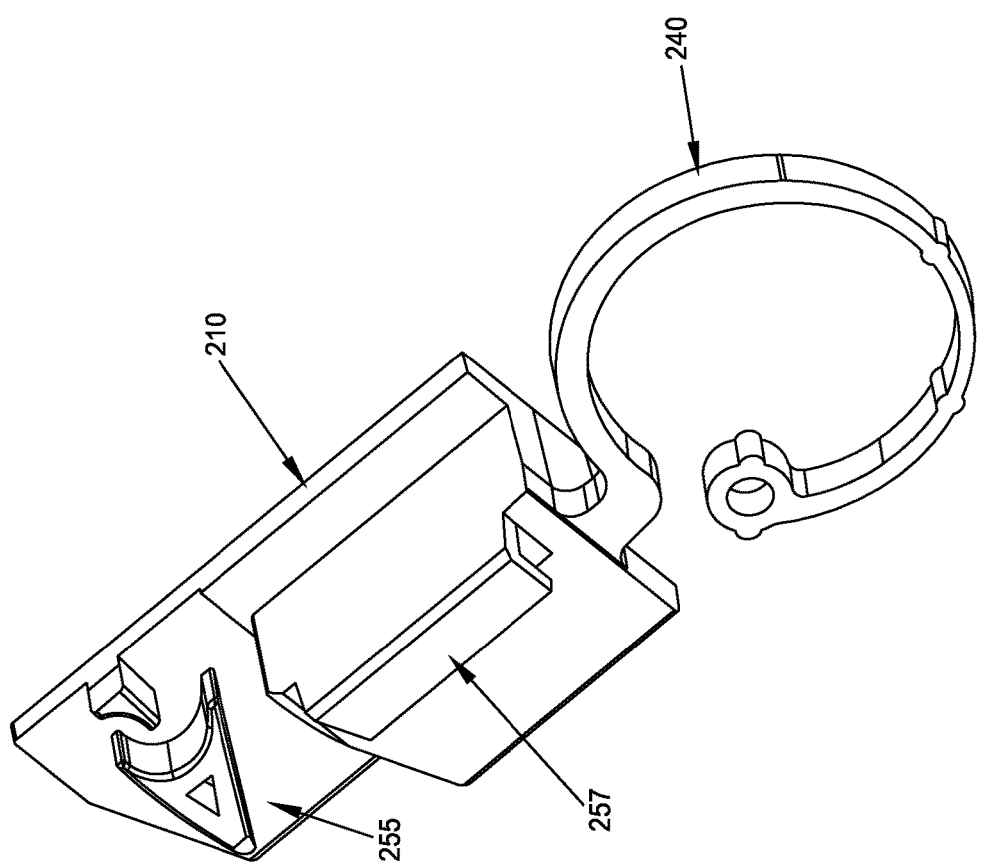

Looking first at FIGS. 1-4, there is shown novel endoscopic cutting forceps 5 which comprise one preferred embodiment of the present invention.

The Novel Endoscopic Cutting Forceps in General

Endoscopic cutting forceps 5 generally comprise a pair of jaws 10 disposed at the distal end of a shaft 15, a blade cutter 20 configured to reciprocate in the space between jaws 10 (and hence cut tissue disposed between the pair of jaws), and a handle 25 disposed at the proximal end of shaft 15 for carrying a lever 30 for actuating the pair of jaws 10 and a trigger 35 for actuating blade cutter 20. Endoscopic cutting forceps 5 preferably allow the pair of jaws 10 and blade cutter 20 to be rotated as a unit about the axis of shaft 15 via a knob 40, and endoscopic cutting forceps 5 preferably allow the pair of jaws 10 to be electrically energized via a button 45 so as to provide electrocautery function to endoscopic cutting forceps 5.

More particularly, and looking now at FIGS. 1-9, jaws 10 are each secured to the distal end 50 of a support rod 55, with support rods 55 and the proximal ends of jaws 10 being disposed within shaft 15. The proximal ends 60 of support rods 55 are secured to a hub 65, which is itself secured to a wall 70 of handle 25. As a result of this construction, jaws 10 are effectively fixed to handle 25. As seen in the figures, jaws 10 are outwardly biased relative to support rods 55, so that the distal ends of jaws 10 naturally diverge from one another. Jaws 10 comprise slots 75 (FIG. 4) which receive blade cutter 20.

Shaft 15 is movable relative to handle 25 so as to selectively close down jaws 10. More particularly, shaft 15 is hollow and is disposed coaxially over the proximal ends of jaws 10 and coaxially over support rods 55. The proximal end of shaft 15 is connected to a mount 80 (FIG. 6) which is engaged by lever 30 as will hereinafter be discussed. Shaft 15 has a flange 85 intermediate its length. A compression spring 90 is disposed about shaft 15 between a wall 95 of handle 25 and flange 85 of shaft 15 so as to spring-bias shaft 15 in the proximal direction. Another compression spring 100 may be disposed about shaft 15 between flange 85 of shaft 15 and a surface of mount 80 so as to bias mount 80 proximally.

As noted above, lever 30 may be used to actuate jaws 10. More particularly, lever 30 is rotatably pinned at 105 to handle 25 so that when the finger grip 110 of lever 30 is pulled proximally toward palm grip 115 of handle 25, the opposing end 120 of lever 30 is moved distally, whereby to move mount 80 distally and thereby move shaft 15 distally. Such distal movement of shaft 15 forces jaws 10 to close. When finger grip 110 of lever 30 is released, compression spring 90 returns shaft 15 proximally, whereby to cause jaws 10 to open. Note that blade cutter 20 is received in slots 75 of jaws 10 when jaws 10 are in their open position and blade cutter 20 is also received in slots 75 of jaws 10 when jaws 10 are in their closed position.

Looking now at FIGS. 1-8, 10 and 11, blade cutter 20 is disposed at the distal end 125 of a drive rod 130, with the proximal end of blade cutter 20 and drive rod 130 being disposed within shaft 15. The proximal end of drive rod 130 is secured to a hub 135.

Trigger 35 actuates blade cutter 20. More particularly, trigger 35 is rotatably pinned at 140 to handle 25 so that when trigger 35 is pulled proximally toward palm grip 115 of handle 25, the opposing end 145 of trigger 35 is moved distally, whereby to move hub 135 distally and thereby move drive rod 130 and blade cutter 20 distally. Note that when jaws 10 are in their closed position and blade cutter 20 is moved distally, blade cutter 20 will ride distally within slots 75 formed in jaws 10.

As noted above, endoscopic cutting forceps 5 preferably allow the pair of jaws 10 and blade cutter 20 to be rotated as a unit about the axis of shaft 15 via a knob 40. To this end, knob 40 drivingly engages mount 80 such that when knob 40 is rotated, mount 80 is also rotated, whereby to rotate hub 65 and thereby rotate support rods 55 and hence jaws 10. Note that inasmuch as blade cutter 20 is received within slots 75 in jaws 10 when jaws 10 are in both their open and closed positions, rotation of jaws 10 will cause blade cutter 20 to rotate in unison with jaws 10.

As also noted above, endoscopic cutting forceps 5 allow the pair of jaws 10 to be electrically energized via a button 45 so as to provide electrocautery function to endoscopic cutting forceps 5. More particularly, and looking now at FIGS. 1-3, 5-9 and 12-16, in the preferred form of the invention, jaws 10 and support rods 55 are formed out of an electrically conductive material, and button 45 is used to activate a switch which connects a power line 150 to jaws 10. As a result, pressing button 45 electrically energizes jaws 10 so as to provide electrocautery function to endoscopic cutting forceps 5. In this respect it should be appreciated that, where shaft 15 is made out of an electrically conductive material, and/or where drive rod 130 is made out of an electrically conductive material, an insulating member 155 is disposed between shaft 15 and support rods 55 and jaws 10, and between drive rod 130 and support rods 55 and jaws 10, so as to avoid inadvertent short-circuiting of the electrical components of endoscopic cutting forceps 5.

Thus it will be seen that endoscopic cutting forceps 5 generally comprise a pair of jaws 10 disposed at the distal end of a shaft 15, a blade cutter 20 configured to reciprocate in the space between jaws 10 (and hence cut tissue disposed between the pair of jaws 10), and a handle 25 disposed at the proximal end of shaft 15 for carrying a lever 30 for actuating the pair of jaws 10 and a trigger 35 for actuating blade cutter 20. Endoscopic cutting forceps 5 preferably allow the pair of jaws 10 and blade cutter 20 to be rotated as a unit about the axis of shaft 15 via a knob 40, and endoscopic cutting forceps 5 preferably allow the pair of jaws 10 to be electrically energized via a button 45 so as to provide electrocautery function to endoscopic cutting forceps 5.

Novel Latching Mechanism

In accordance with the present invention, there is also provided a novel latching mechanism for the lever which actuates the jaws, whereby to allow the jaws to be temporarily locked (or clamped) in a closed position about tissue while the blade cutter is actuated to cut the tissue disposed between the clamped jaws.

Significantly, the latching mechanism of the present invention is mechanically simple and hence easy and inexpensive to manufacture.

In addition, the latching mechanism of the present invention may also be used for the actuating levers of other surgical instruments and/or other lever-actuated devices wherein the latching mechanism is mechanically simple and hence easy and inexpensive to manufacture.

Looking next at FIGS. 1-3, 5-7, 9-11 and 17-26, there is shown a latching mechanism 200 which comprises one preferred form of the present invention. Latching mechanism 200 generally comprises a selector plate 205 and a latch plate 210.

Selector plate 205 serves to selectively position latch plate 210 within handle 25. Selector plate 205 is movably mounted to handle 25, and latch plate 210 is mounted to selector plate 205, such that, by adjusting the position of support plate 205 within handle 25, the position of latch plate 210 may also be adjusted within handle 25. In this way selector plate 205 can be used to selectively position latch plate 210 in a "latch operative position" or in a "latch inoperative position" within handle 25, as will hereinafter be discussed.

More particularly, selector plate 205 is slidably mounted to handle 25 of endoscopic cutting forceps 5. A thumb button 215 protrudes through a window 220 formed in handle 25 so that the user can adjustably position selector plate 205 (and hence adjustably position latch plate 210) within handle 25. Detents 225 are formed in selector plate 205 and cooperate with a protrusion 230 formed on handle 25 whereby to allow selector plate 225 to be maintained in a "latch operative position" or in a "latch inoperative position" within handle 25 until urged otherwise by the user.

Figure 24:
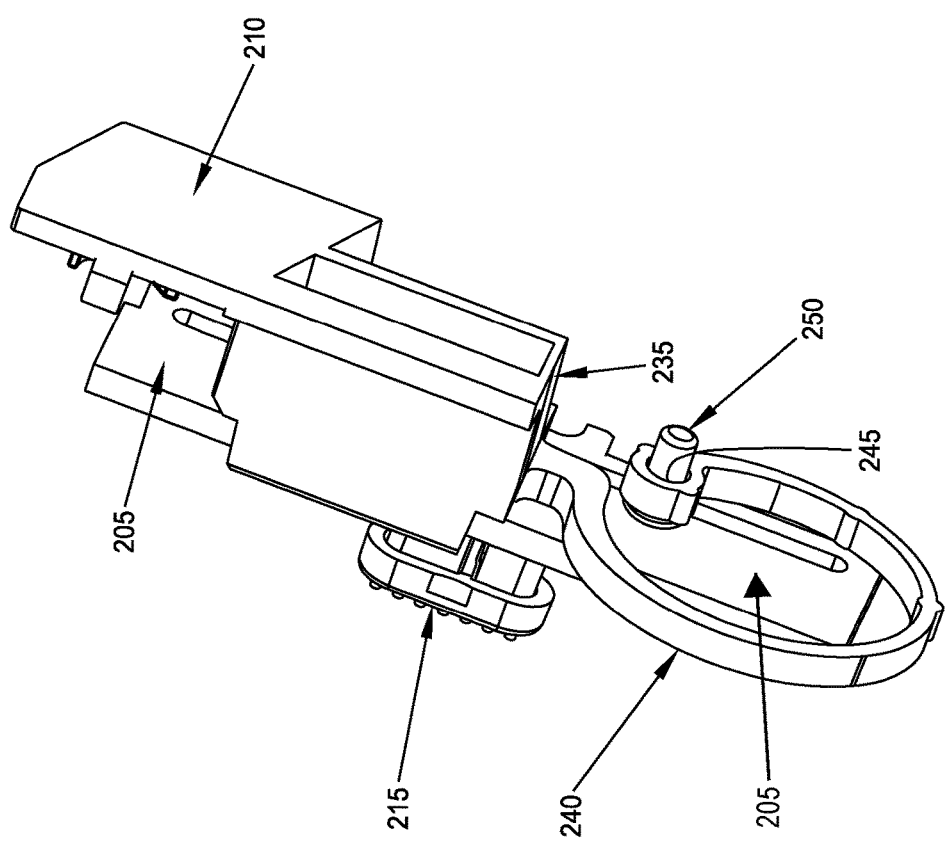
Figure 25:
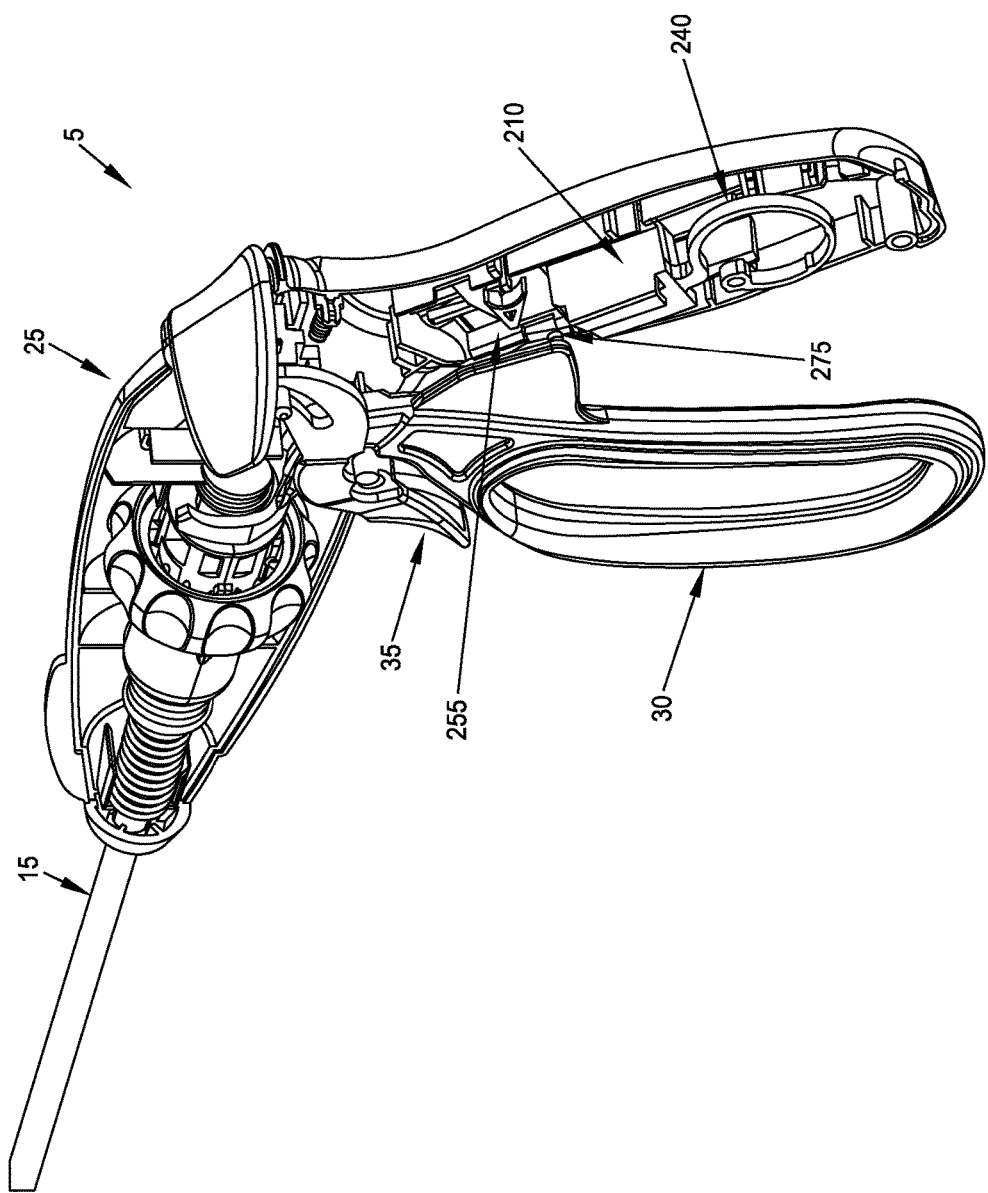

Latch plate 210 is slidably mounted to selector plate 205. More particularly, latch plate 210 comprises a body 235 having a loop spring 240 extending therefrom (FIG. 24). In one preferred form of the invention, loop spring 240 is formed integral with body 235. Loop spring 240 comprises a bore 245 which is mounted on a pin 250 of selector plate 205. Loop spring 240 biases body 235 of latch plate 210 into a given position on selector plate 205, but permits body 235 of latch plate 210 to be slidably moved on selector plate 205 (both towards and away from pin 250 on selector plate 205) against the power of loop spring 240. In one preferred form of the invention, latch plate 210 moves linearly with respect to handle 25 as latch plate 210 moves on selector plate 205. Body 235 of latch plate 210 includes a flange 257 which is slidably mounted on selector plate 205, whereby to stabilize latch plate 210 as it moves on selector plate 205. As a result of this construction, body 235 of latch plate 210 can be urged away from pin 250 of selector plate 205 against the power of loop spring 240, or body 235 of latch plate 210 can be urged toward pin 250 of selector plate 205 against the power of loop spring 240.

Figure 26:
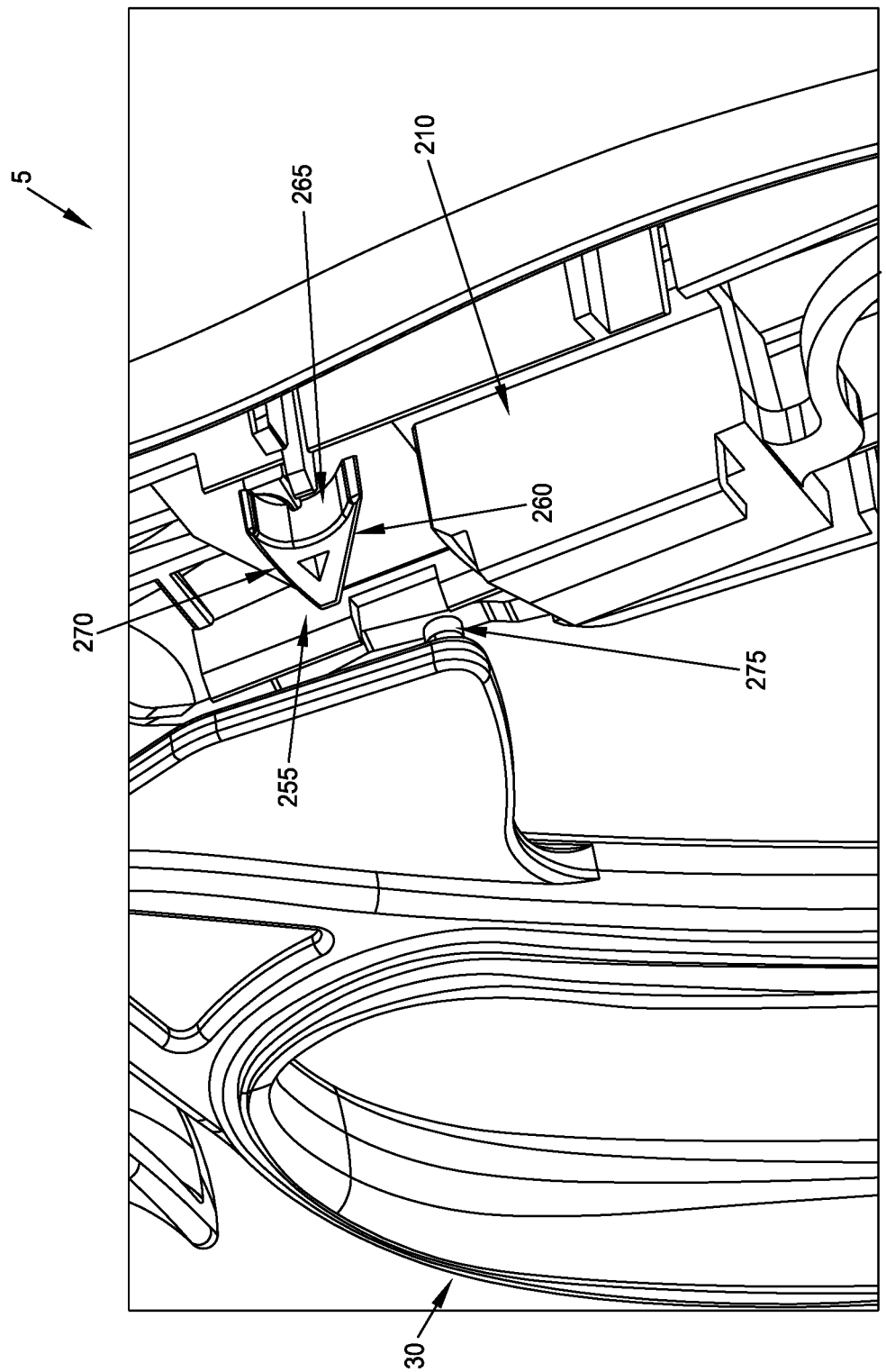
Figure 27:
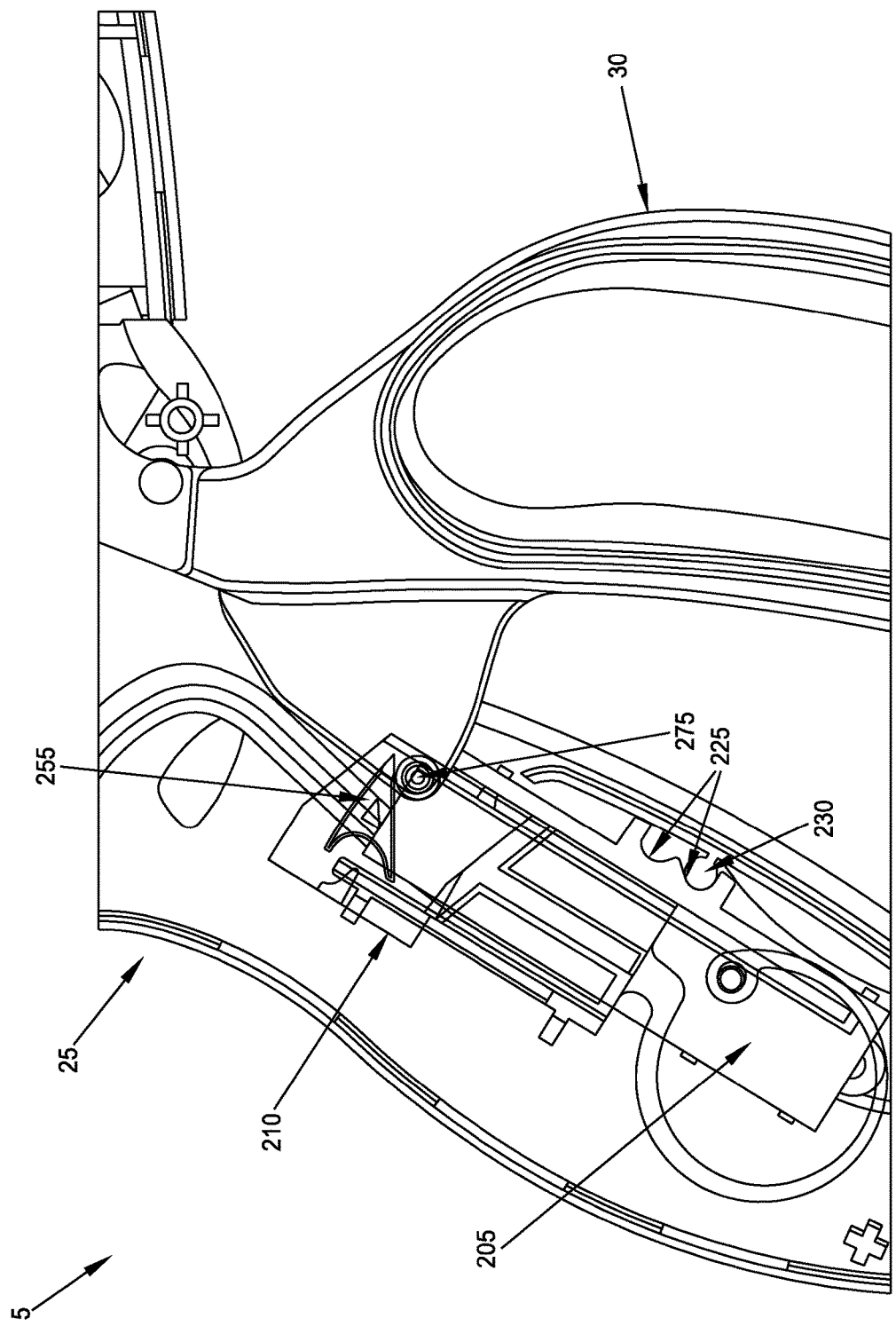
FIGS. 27-38 are schematic views showing exemplary operation of the novel jaw clamp lever latching mechanism of the endoscopic cutting forceps of FIGS. 1-26.
Figure 28:
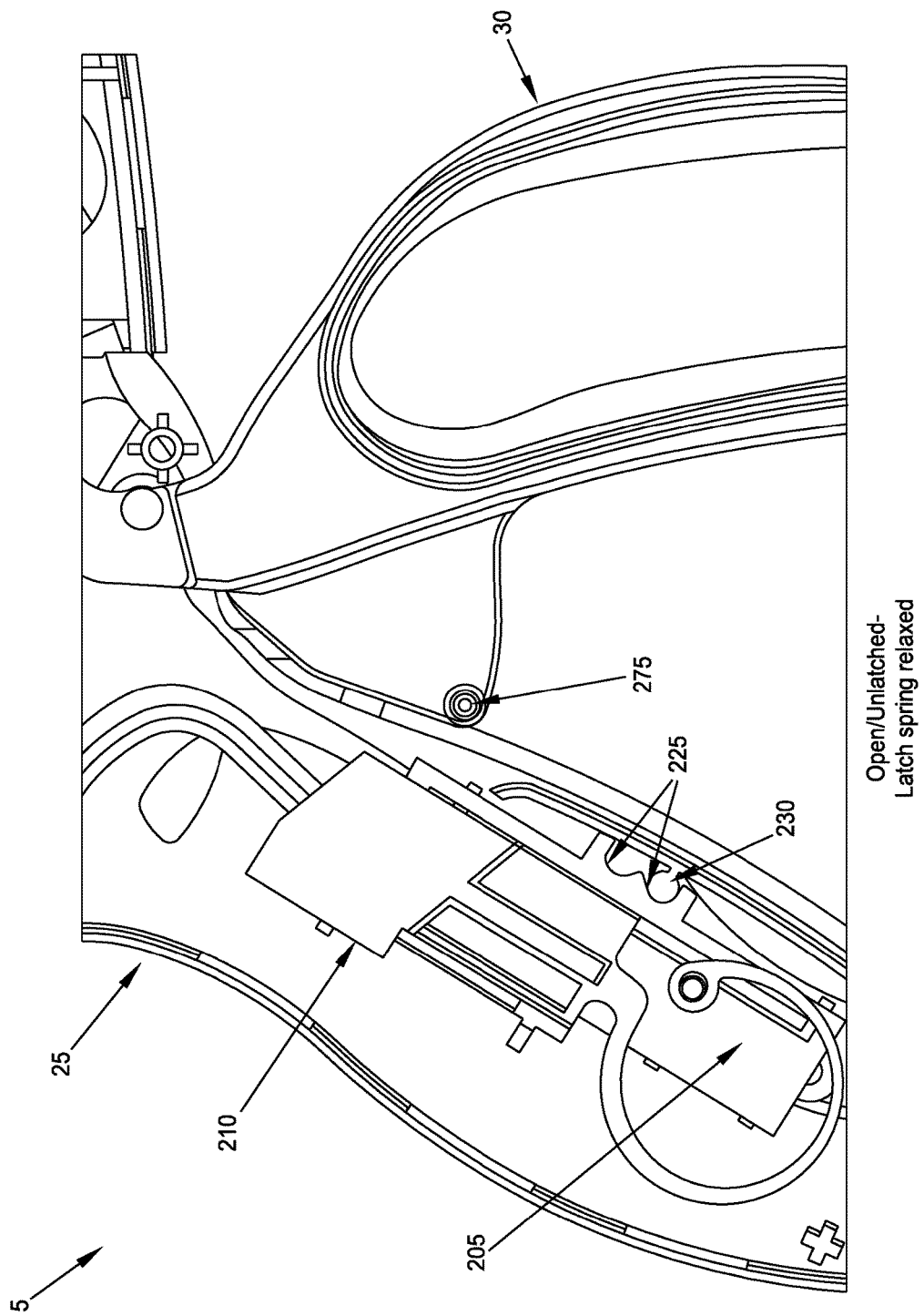
Figure 29:
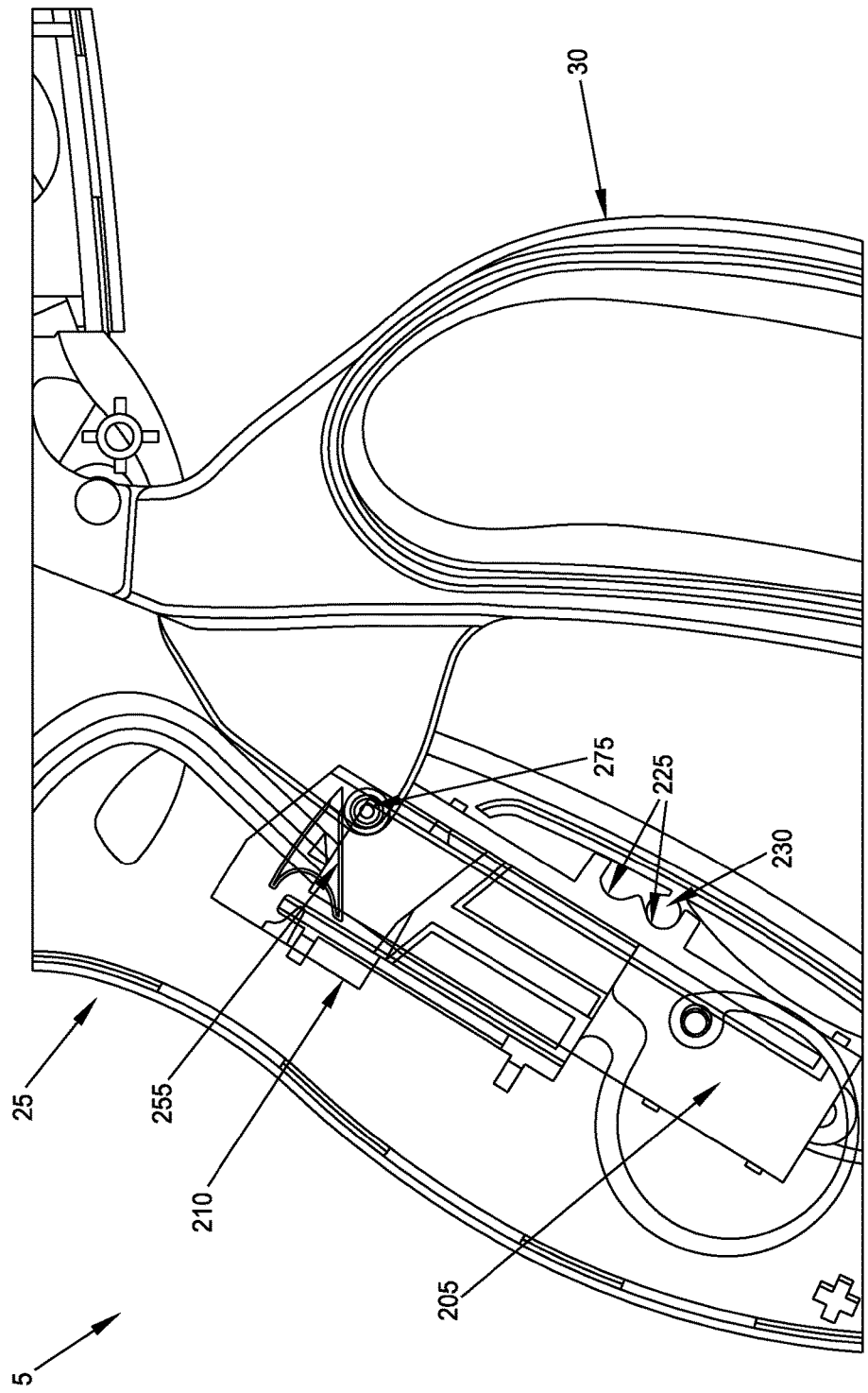
Figure 30:
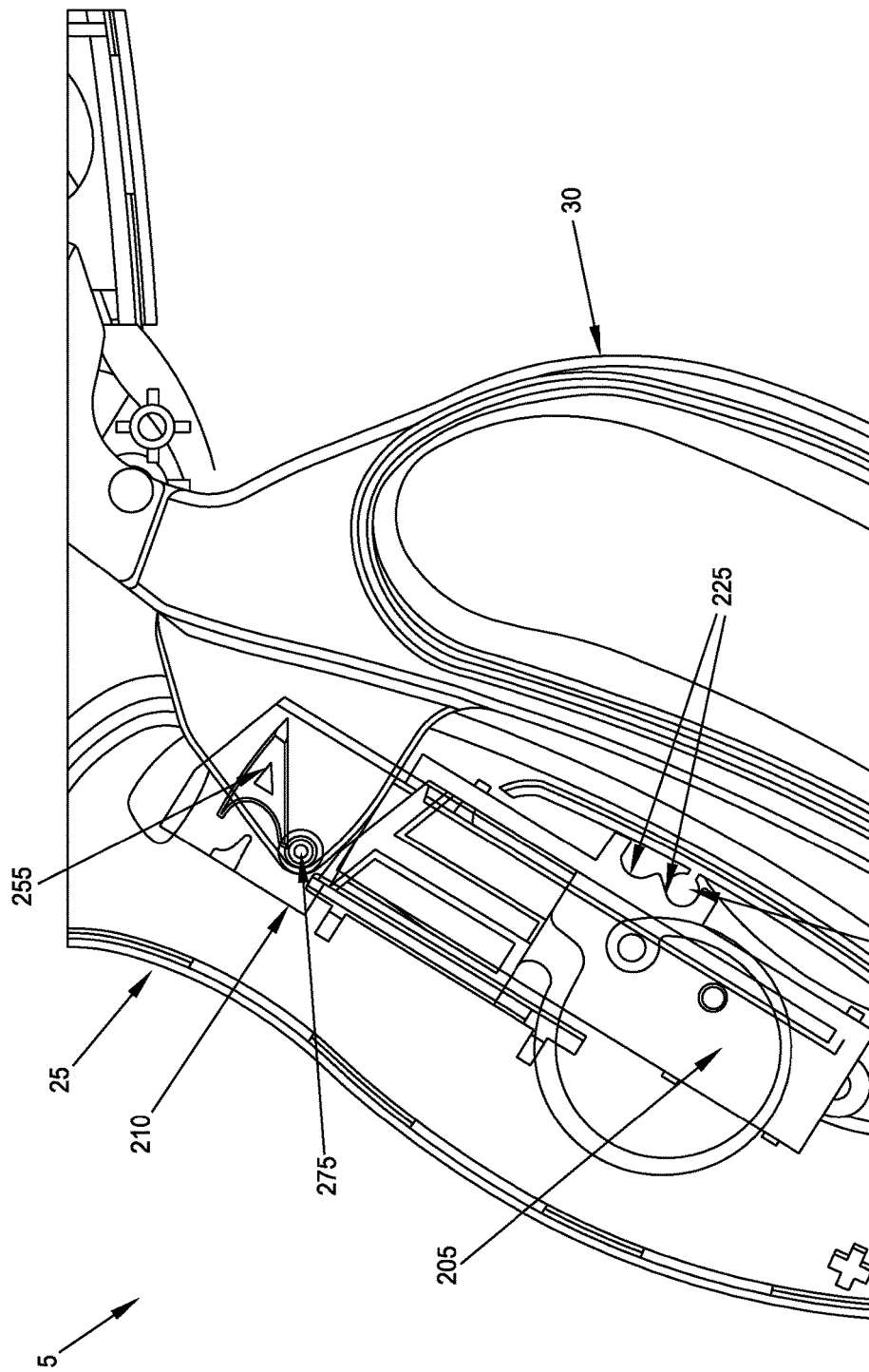
Figure 31:
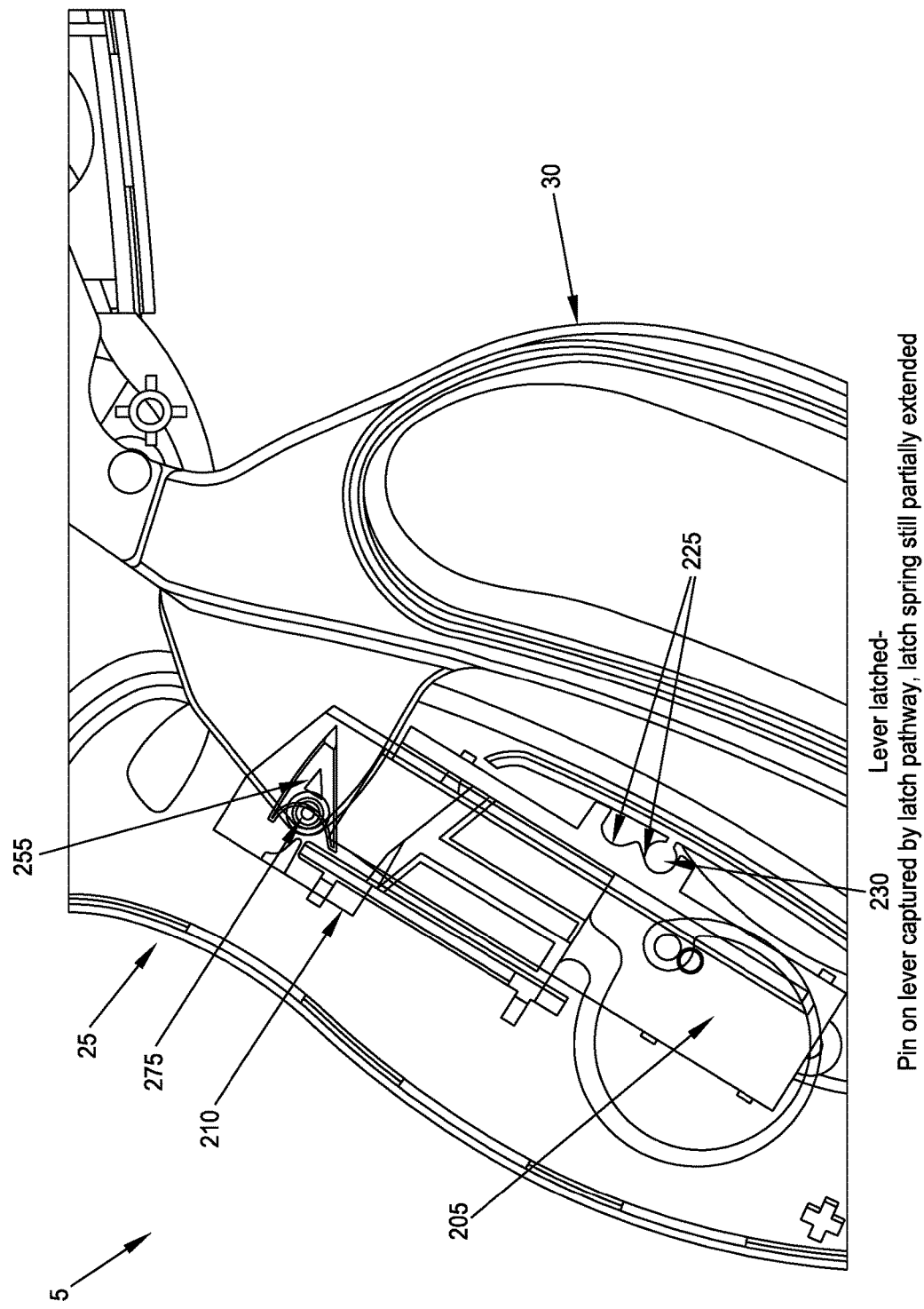
Figure 32:
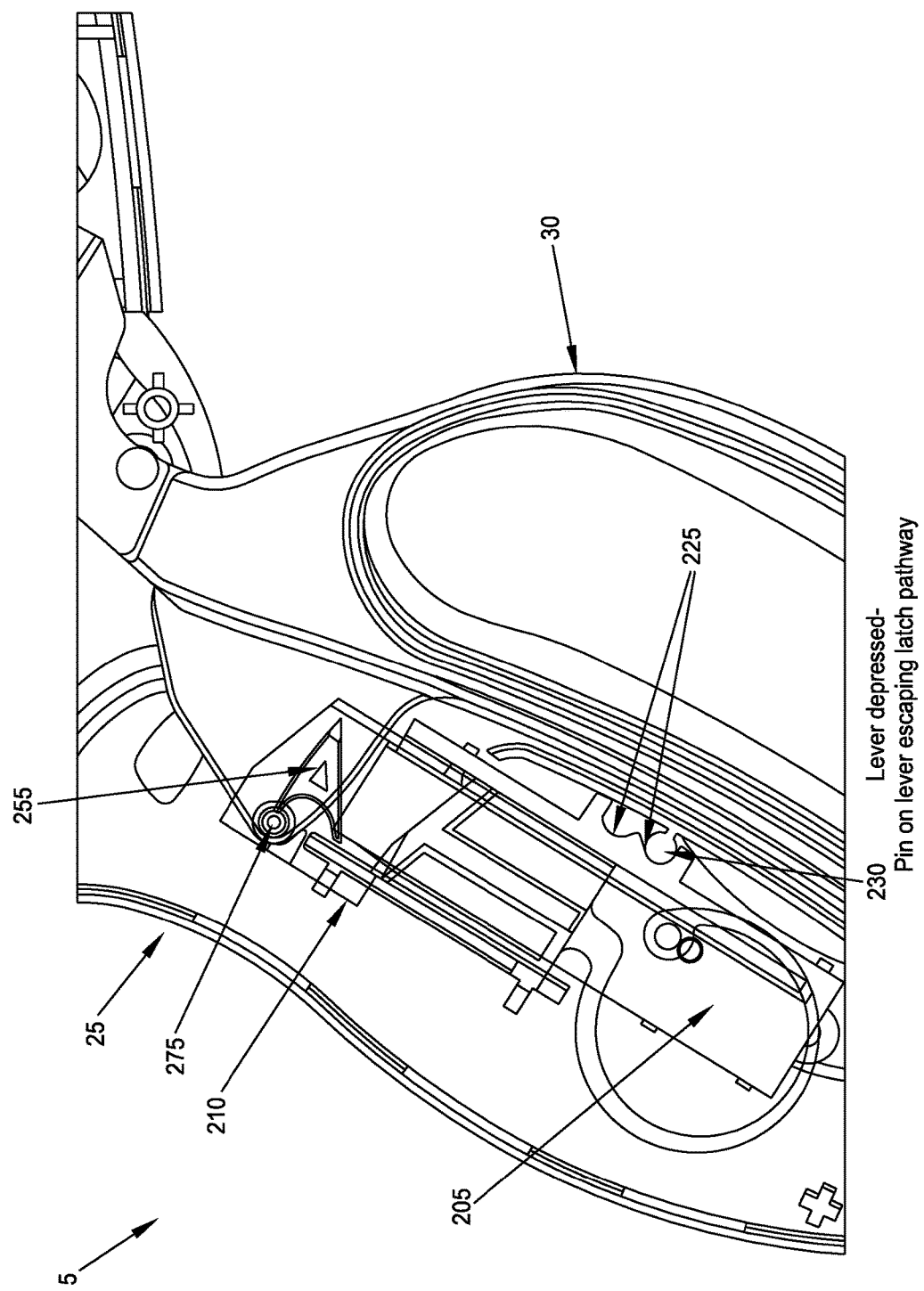
Figure 33:
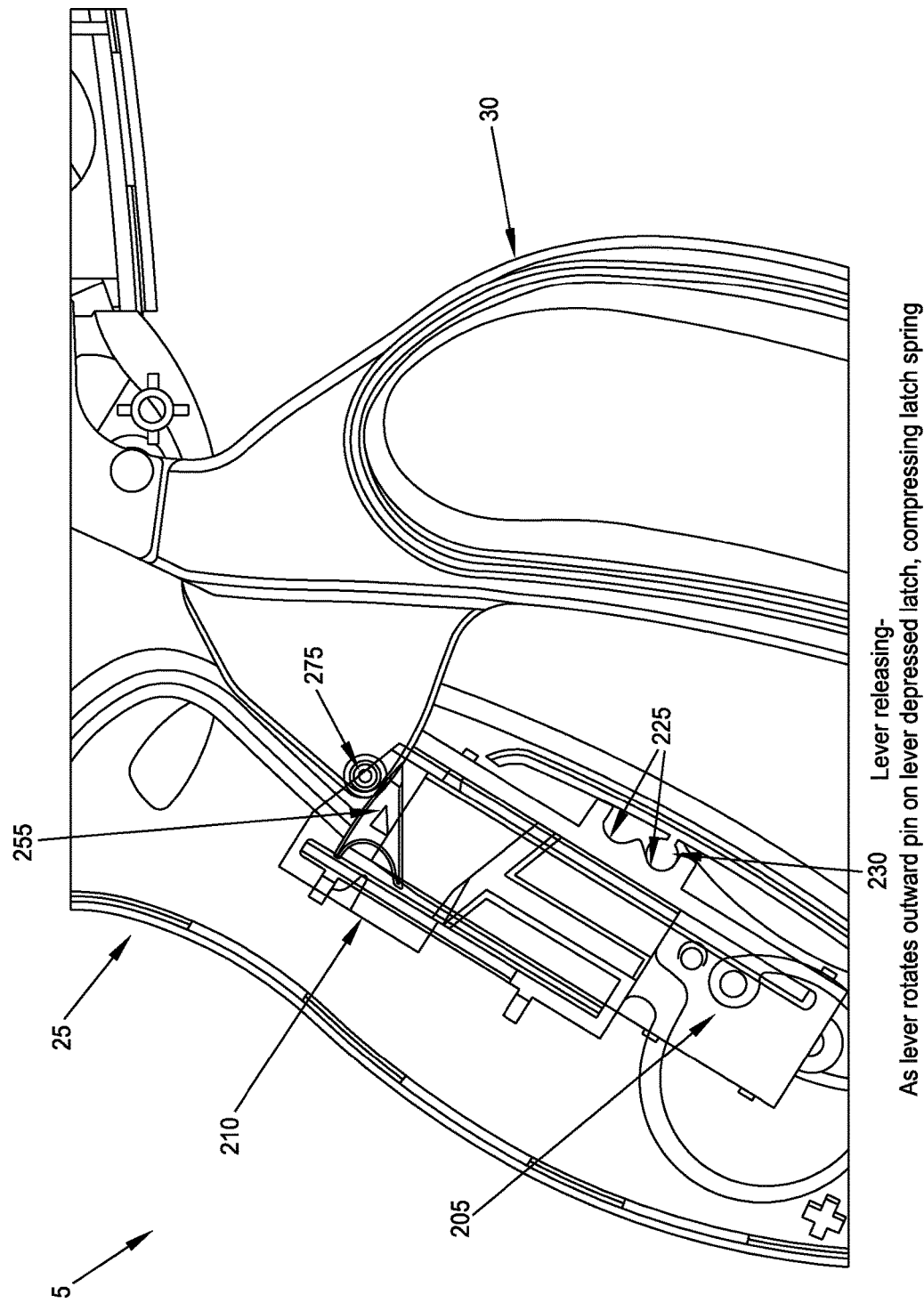
Figure 34:
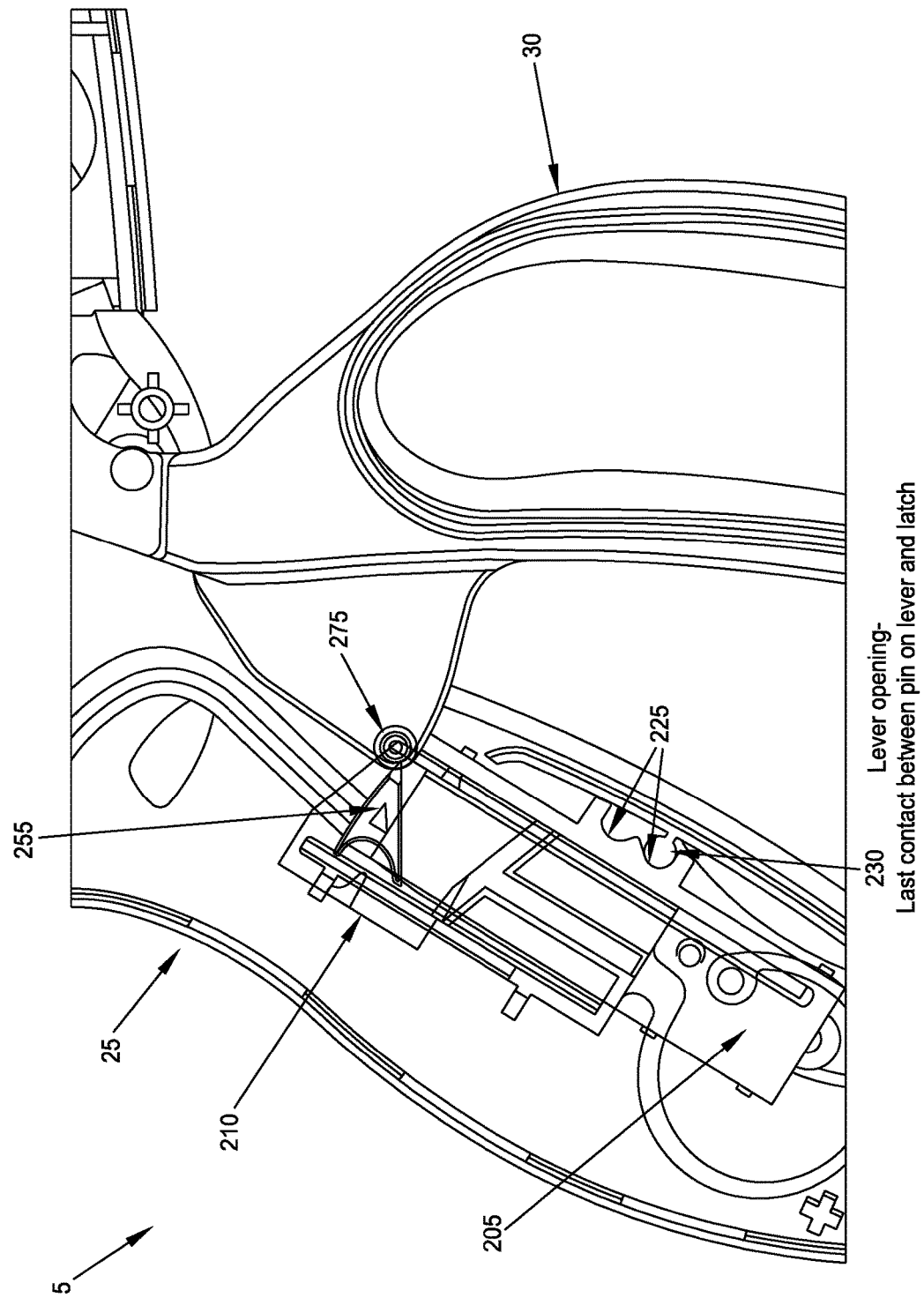
Figure 35:
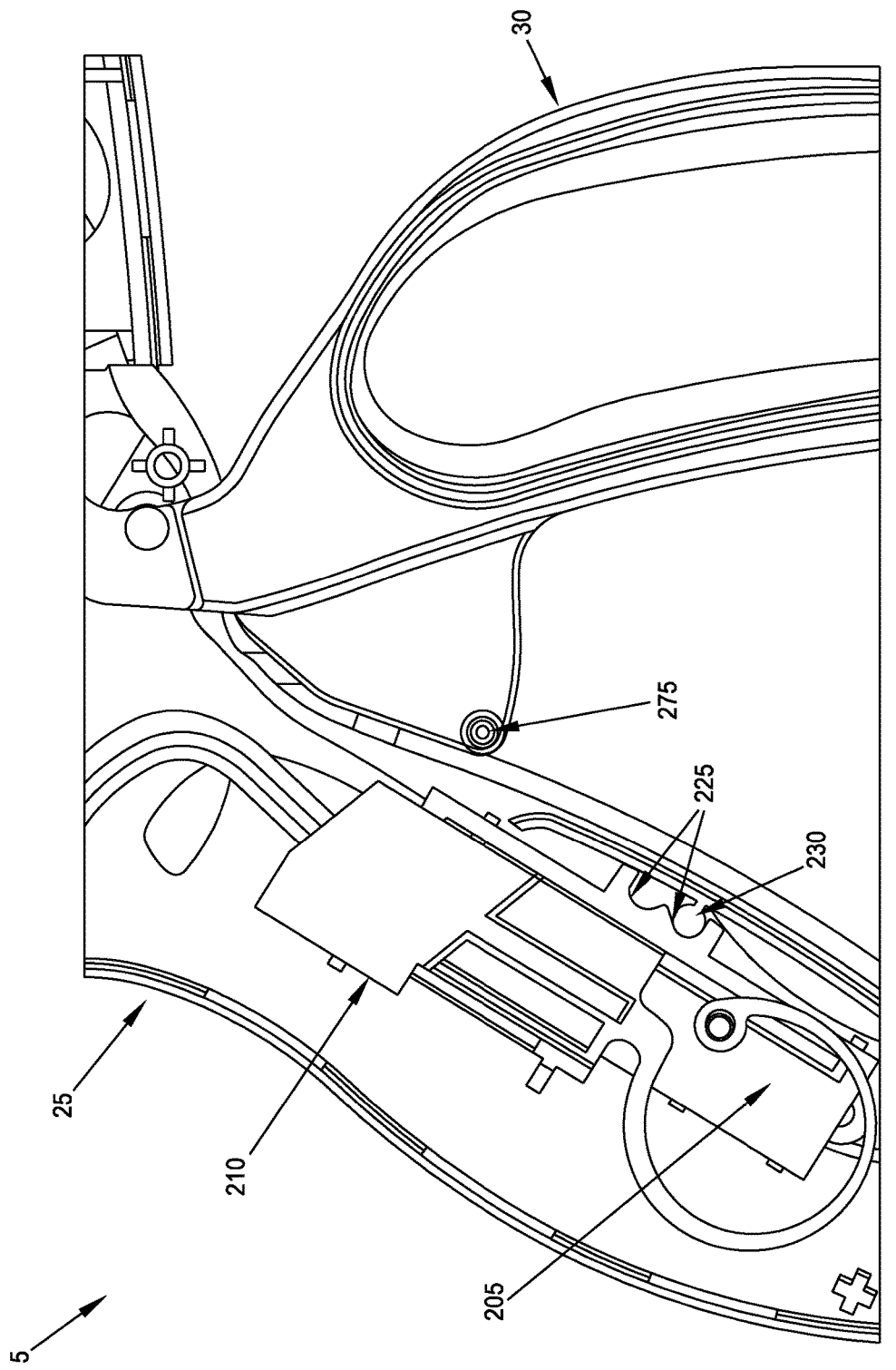

A latch element 255 is mounted to body 235 of latch plate 210. In one preferred form of the invention, latch element 255 is formed integral with body 235 of latch plate 210. Latch element 255 comprises a first surface 260, a second surface 265, and a third surface 270 (FIG. 26). In one preferred form of the invention, first surface 260 comprises a substantially linear configuration, second surface 265 comprises a concave configuration, and third surface 270 comprises a slightly convex or substantially linear configuration.

First surface 260, second surface 265 and third surface 270 together define a labyrinth (i.e., a non-linear track comprising a leading first surface 260, a concave second surface 265, and a trailing third surface 270, whereby to form a tortuous path with a concavity intermediate its length), and interact with a latch pin 275 (FIG. 26) formed on lever 30, so as to provide the desired latching function.

More particularly, when selector plate 205 is appropriately positioned within handle 25 so that the apparatus is configured in the "latch operative position", and when lever 30 is thereafter pulled toward palm grip 115 of handle 25 (i.e., so as to close jaws 10), latch pin 275 engages first surface 260 of latch element 255 and forces latch plate 210 away from pin 250, against the power of loop spring 240. Latch pin 275 rides along first surface 260 of latch element 255 until latch pin 275 reaches the end of first surface 260, whereupon latch pin 275 moves onto second surface 265 of latch element 255. As soon as latch pin 275 moves onto the concave second surface 265, loop spring 240 pulls body 235 of latch plate 210 back toward pin 250, until latch pin 275 seats at the base of concave second surface 265. At this point, lever 30 will be maintained in this position (i.e., the "latched" position, with jaws 10 clamped) until lever 30 is thereafter pulled again. More particularly, when it is thereafter desired to unclamp jaws 10, lever 30 is pulled again, against the power of loop spring 240, so as to cause latch pin 275 to move out of the base of concave second surface 265 of latch element 255 and further along concave second surface 265. As soon as latch pin 275 clears the end of concave second surface 265 and moves onto third surface 270 of latch element 255, loop spring 240 pulls latch plate 210 back toward pin 250, until latch pin 275 is returned to its original starting position clear of third surface 270. At this point, lever 30 will have been returned to its original starting position, pending a further cycling of endoscopic cutting forceps 5.

It will be appreciated that the latching function just described relies upon the interaction of latch pin 275 with latch element 255. It will also be appreciated that selector plate 205 allows the position of latch plate 210 to be adjusted within handle 25. Thus selector plate 205 provides the ability to render the latching function operative or inoperative by adjusting the position of latch plate 210 (and hence the position of latch element 255) vis-à-vis the position of lever 30 (and hence the orbit of latch pin 275). More particularly, by positioning selector plate 205 so that the position of latch element 255 is outside the orbit of latch pin 275, the selector plate can be used to put the apparatus in a "latch inoperative position". Conversely, by positioning selector plate 205 so that the position of latch element 255 is within the orbit of latch pin 275, the selector plate can be used to put the apparatus in a "latch operative position". The user adjusts the position of selector plate 205 using thumb button 215.

Figure 36:
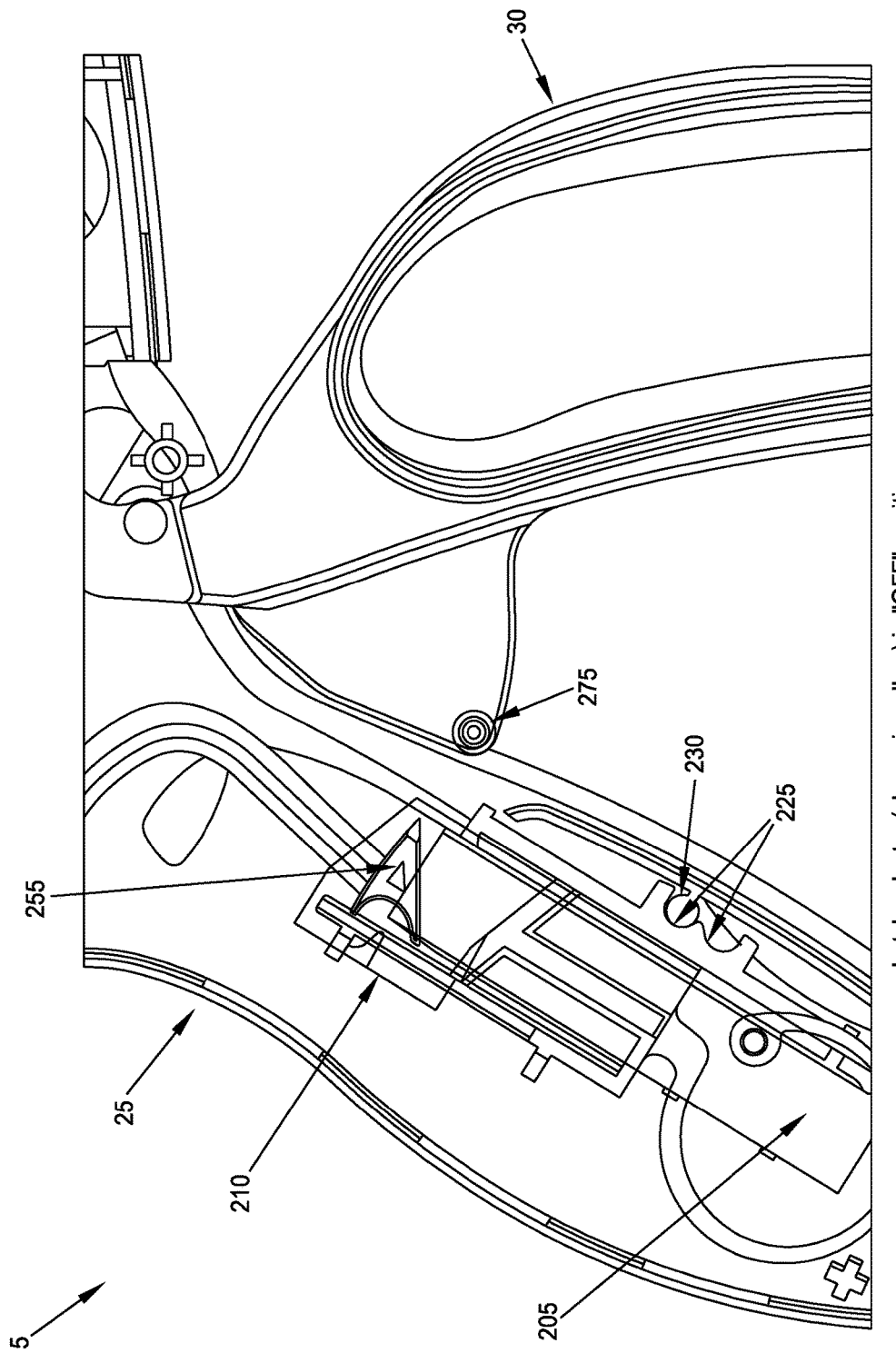
Figure 37:
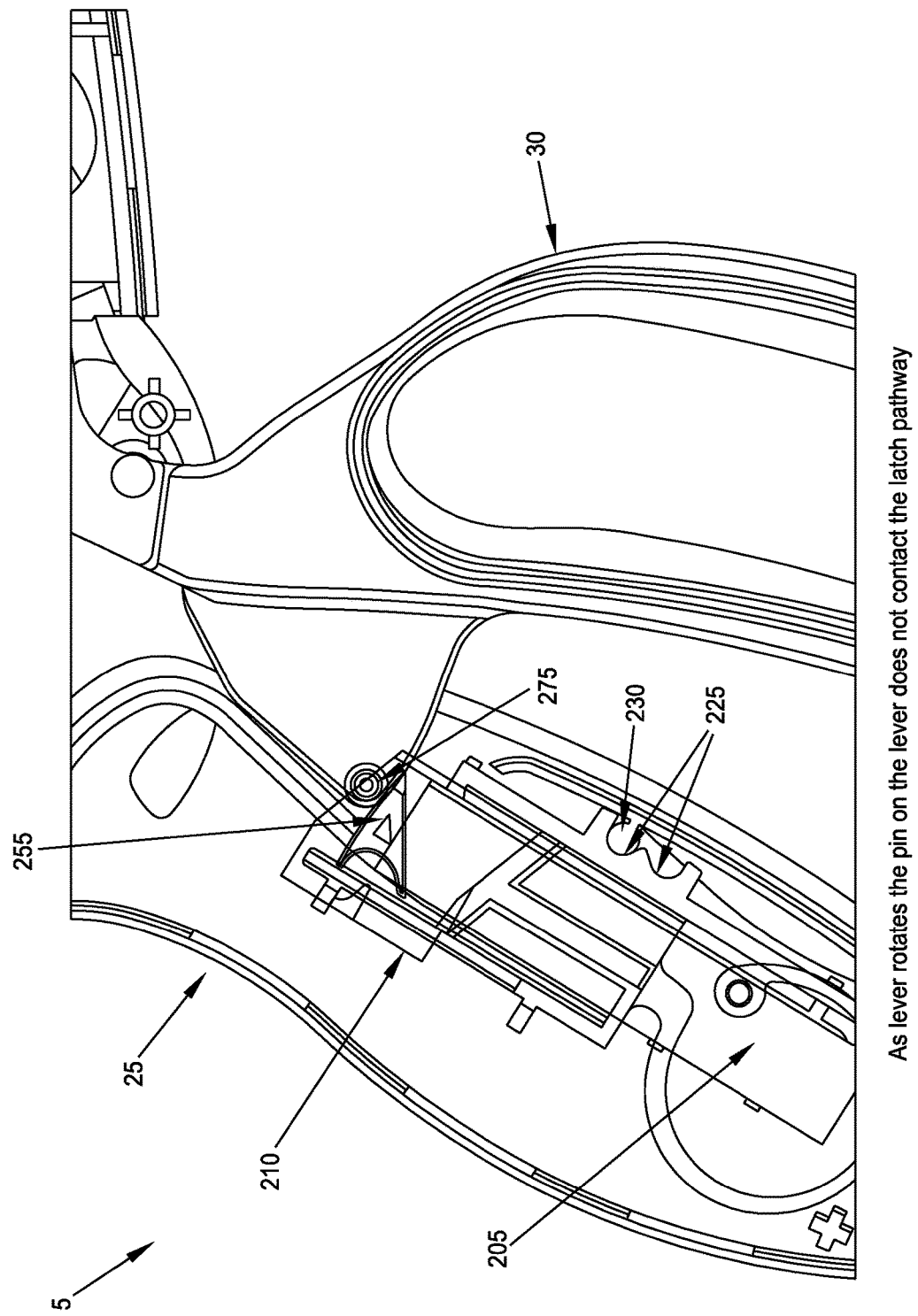
Figure 38:
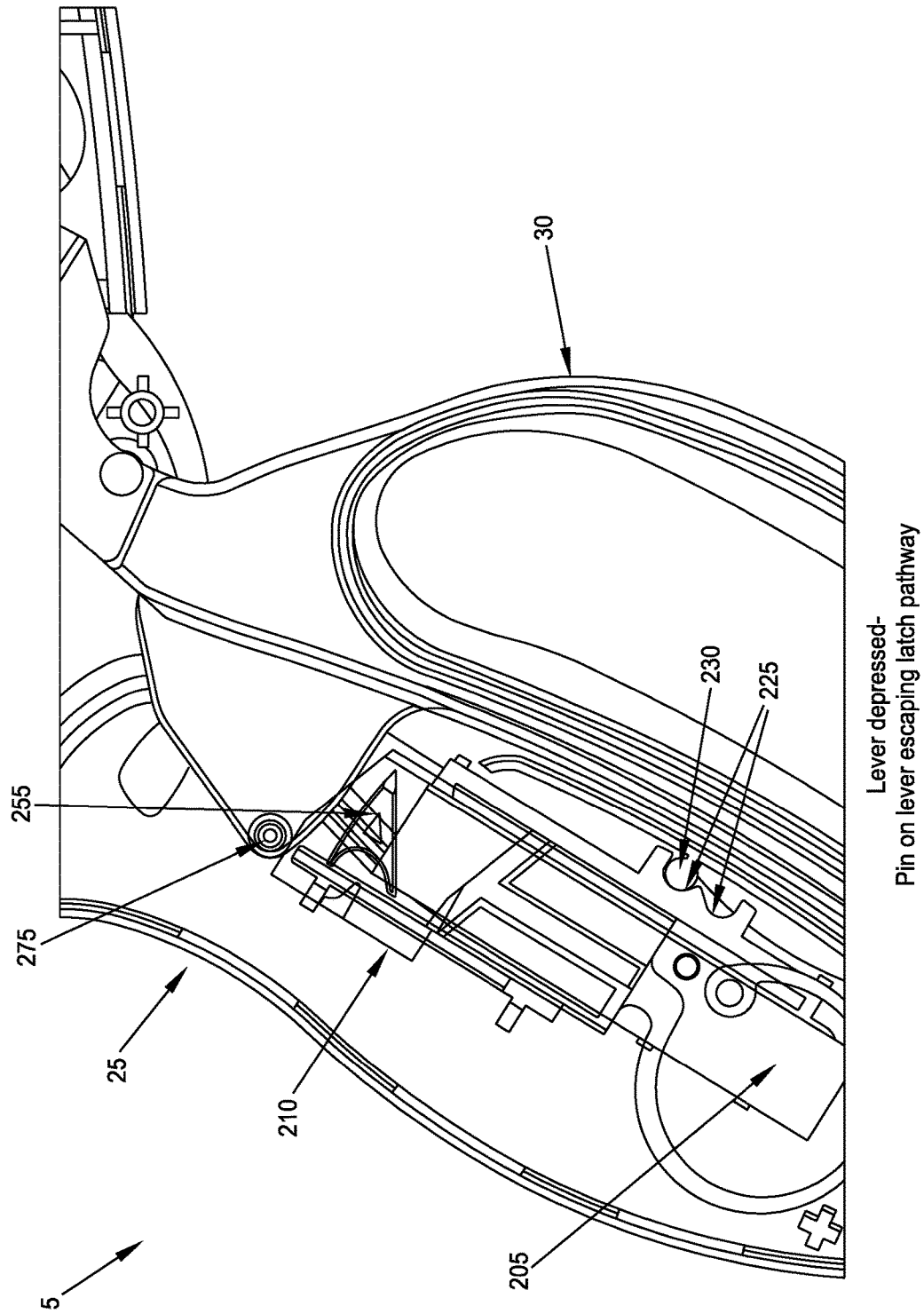

Exemplary Operation Of The Novel Latching Mechanism Of The Endoscopic Cutting Forceps FIGS. 27-38 illustrate operation of the endoscopic cutting forceps 5 (note that the specific constructions shown in FIGS. 27-38 may differ slightly from the specific constructions shown in FIGS. 1-26, however, FIGS. 27-38 depict a common operation of the latching function of the present invention). More particularly, FIGS. 27-35 show endoscopic cutting forceps 5 with selector plate 205 set in the "latch operative position" and with the apparatus cycling through a complete latching/unlatching operation. FIGS. 36-38 show endoscopic cutting forceps 5 with selector plate 205 set in the "latch inoperative position" and with lever 30 cycling through a complete "pull and release" operation.

Alternative Preferred Embodiments

In the preceding description, lever 30 is described as being rotatably pinned to handle 25 at 105. However, it should be appreciated that other connections may also be employed. By way of example but not limitation, lever 30 may be movably mounted to handle 25 by the legs of a so-called "4-bar" mechanism.

It should be appreciated that, if desired, selector plate 205 may move in a direction which is different than the direction of movement of latch plate 210, provided, however, that movement of selector plate 205 moves latch plate 210 into, and out of, the orbit of latch pin 275. By way of example but not limitation, selector plate 205 could move in a direction perpendicular to the direction of movement of latch plate 210, whereby to move latch plate 210 into, and out of, the orbit of latch pin 275.

If desired, latch plate 210 may be movably mounted to selector plate 205 by a variety of means, so as to provide a variety of different movements, e.g., linear movement, pivoting movement, prescribed motion such as by a so-called "4-bar" mechanism, traversing in an arcuate track, etc.

Thus it will be seen that the present invention provides a new and improved latching mechanism for an endoscopic cutting forceps wherein the latching mechanism is mechanically simple and hence easy and inexpensive to manufacture.

It will also be appreciated that the new and improved latching mechanism of the present invention may be used in conjunction with the actuating levers of other surgical instruments and/or other lever-actuated devices, whereby to provide a latching mechanism which is mechanically simple and hence easy and inexpensive to manufacture.

Modifications Of The Preferred Embodiments

It will be appreciated that various modifications may be made to the preferred embodiments discussed above without departing from the scope of the present invention.

Thus, for example, the locations of selector plate 205/latch plate 210 and latch pin 275 may be reversed, i.e., selector plate 205 and latch plate 210 may be mounted on lever 30 and latch pin 275 may be mounted on handle 25.

By way of further example but not limitation, selector plate 205 may be omitted, in which case latch plate 210 is slidably mounted directly to handle 25 (or, if the location of latch plate 210 and latch pin 275 are reversed, slidably mounted directly to lever 30). Of course, in this form of the invention, the apparatus is always set in the "latch operative position" and is incapable of being set in the "latch inoperative position".

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A lever latching system comprising:
a housing;
a lever having a latch pin fixedly mounted to said lever, said lever being movably mounted to said housing so that said latch pin moves in an arc; and
a latch plate movably mounted to said housing such that said latch plate moves linearly when said latch plate is engaged by said latch pin, said latch plate comprising a labyrinth for receiving said latch pin.

2. A lever latching system according to claim 1 further comprising a spring for biasing said latch plate with respect to said housing, wherein said spring can both extend and compress during reciprocal movement of said latch plate, and further wherein said spring is loop-shaped.

3. A lever latching system according to claim 1 further comprising a spring for biasing said latch plate with respect to said housing, wherein said spring is formed integral with said latch plate.

4. A lever latching system according to claim 1 wherein said latch plate is movably mounted to a selector plate, and further wherein said selector plate is movably mounted to said housing.

5. A lever latching system according to claim 4 wherein said selector plate is movable between (i) an engaged position wherein said labyrinth of said latch plate intersects said arc of said latch pin, and (ii) a disengaged position wherein said labyrinth of said latch plate does not intersect said arc of said latch pin.

6. A lever latching system according to claim 4 further comprising a spring for biasing said latch plate with respect to said selector plate.

7. A lever latching system according to claim 6 wherein said spring is formed integral with said latch plate.

8. A latching system comprising:
a first unit;
a second unit comprising a latch pin, said second unit being movably mounted to said first unit so that said latch pin moves in a prescribed motion;
a selector plate movably mounted to said first unit; and
a latch plate comprising a labyrinth for selectively receiving said latch pin, said latch plate being movably mounted to said selector plate;
wherein said latch plate moves linearly relative to said selector plate.

9. A latching system according to claim 8 wherein said selector plate is movable between (i) an engaged position wherein said labyrinth of said latch plate is engagable by said latch pin of said second unit, and (ii) a disengaged position wherein said labyrinth of said latch plate is not engageable by said latch pin of said second unit.

10. A latching system according to claim 8 wherein said prescribed motion is arcuate motion.

11. A latching system according to claim 8 further comprising a spring for biasing said latch plate with respect to said selector plate.

12. A latching system according to claim 11 wherein said spring is formed integral with said latch plate.

13. A latching system according to claim 8 further comprising a spring for biasing said latch plate with respect to said first unit.

14. A latching system comprising:
a first member;
a second member comprising a latch pin, said second member being movably mounted to said first member so that said latch pin moves in a prescribed motion;
a selector plate movably mounted to said first member;
a latch plate movably mounted to said selector plate and comprising a labyrinth for selectively receiving said latch pin;
a spring secured to said selector plate and engaging said latch plate for biasing said latch plate with respect to said selector plate;
wherein said selector plate moves said latch plate between an engaged position wherein said labyrinth intersects said prescribed motion and a disengaged position wherein said labyrinth does not intersect said prescribed motion.

15. A latching system according to claim 14 wherein said spring is formed integral with said latch plate for biasing said latch plate relative to said selector plate.

16. A latching system according to claim 14 wherein said latch plate moves linearly with respect to said selector plate.

17. A latching system comprising:
a first unit;
a second unit;
said first unit and said second unit being movably mounted relative to one another;
a latch pin fixedly mounted to one of said first unit and said second unit; and
a latch plate movably mounted to the other of said first unit and said second unit such that said latch plate moves non-linearly and non-pivotally with respect to said other of said first unit and said second unit when said latch plate is engaged by said latch pin, said latch plate comprising a labyrinth for receiving said latch pin.

18. A latching system comprising:
a first unit;

a second unit comprising a latch pin, said second unit being movably mounted to said first unit so that said latch pin moves in a prescribed motion;

a selector plate movably mounted to said first unit; and a latch plate comprising a labyrinth for selectively receiving said latch pin, said latch plate being movably mounted to said selector plate;

wherein said latch plate comprises an integral spring for biasing said latch plate relative to said first unit.

\* \* \* \* \*